United States Patent [19]

Hefner, Jr. et al.

[11] Patent Number: 5,637,669

[45] Date of Patent: Jun. 10, 1997

[54] EPOXY RESINS CONTAINING DISCOTIC MESOGENIC MOIETIES

[75] Inventors: Robert E. Hefner, Jr.; Jimmy D. Earls, both of Lake Jackson, Tex.

[73] Assignee: The Dow Chemical Company, Midland, Mich.

[21] Appl. No.: 436,399

[22] PCT Filed: Oct. 26, 1993

[86] PCT No.: PCT/US93/10196

§ 371 Date: May 18, 1995

§ 102(e) Date: May 18, 1995

[87] PCT Pub. No.: WO94/12556

PCT Pub. Date: Jun. 9, 1994

Related U.S. Application Data

[63] Continuation-in-part of Ser. No. 981,627, Nov. 25, 1992, abandoned.

[51] Int. Cl.$^6$ .................... C07D 303/16; C07D 303/26; C07D 303/27

[52] U.S. Cl. ............................................................. 528/97

[58] Field of Search ........................... 528/97, 98, 99, 528/100, 101, 102; 549/543, 544, 545, 546

[56] References Cited

U.S. PATENT DOCUMENTS

| | | | |
|---|---|---|---|
| 4,764,581 | 8/1988 | Müller et al. | 528/100 |
| 4,865,762 | 9/1989 | Krueder et al. | 252/299.01 |
| 4,908,424 | 3/1990 | Dewhirst et al. | 528/97 |
| 4,954,583 | 9/1990 | Wang | 525/507 |
| 4,992,488 | 2/1991 | Ruf | 523/428 |
| 5,037,934 | 8/1991 | Yasuda et al. | 528/72 |
| 5,128,060 | 7/1992 | Rolfe et al. | 525/507 |
| 5,128,061 | 7/1992 | Kajiwara et al. | 525/523 |
| 5,128,074 | 7/1992 | Nordmann et al. | 528/96 |
| 5,164,464 | 11/1992 | Hefner, Jr. et al. | 525/531 |
| 5,274,092 | 12/1993 | Keinan | 544/525 |

FOREIGN PATENT DOCUMENTS

| | | | |
|---|---|---|---|
| 0030879A1 | 6/1981 | European Pat. Off. | C09K 3/34 |
| 0254865A2 | 2/1988 | European Pat. Off. | C07C 69/62 |
| 0385329A2 | 9/1990 | European Pat. Off. | C09K 19/38 |
| 0405713A1 | 1/1991 | European Pat. Off. | C08F 220/30 |
| 0473935A2 | 3/1992 | European Pat. Off. | C08G 59/50 |
| 0503764A2 | 9/1992 | European Pat. Off. | C07D 303/24 |
| 1268715A | 10/1989 | Japan | C08G 59/32 |
| 591471 | 2/1978 | U.S.S.R. | C07D 303/16 |
| 086/03507 | 6/1986 | WIPO | C08L 63/00 |
| 92/06128 | 4/1992 | WIPO | C08G 59/08 |

OTHER PUBLICATIONS

Derwent Abstract 87-338224 (JP 62-242953, 87-10-23).
Derwent Abstract 89-359920/49 (JP 1 268 715, 26-10-89).
Derwernt Abstract 90-336094/85 (DE 3914376-A, 90-10-31.
Japanese Abstract vol. 14, No. 77 (JP 12-094791).
V. Perec, et al., Macromolecules, 25, pp. 1164-1176 (1992).
H. Lee and K. Neville, "Handbook of Epoxy Resins", McGraw-Hill, New York (1967).

*Primary Examiner*—D. R. Wilson

[57] ABSTRACT

Thermosettable resins, including epoxy resins, polythiirane resins and vinyl ester resins were prepared from compounds containing one or more discotic mesogenic moieties. The resultant thermosettable resins may be processed to provide the discotic liquid crystalline state. The thermosettable resin compositions can be employed in coating, casting, encapsulation, electronic or structural laminate or composite, filament winding, molding and the like applications.

2 Claims, No Drawings

EPOXY RESINS CONTAINING DISCOTIC MESOGENIC MOIETIES

This is a continuation under 371 of PCT/US93/10,196 filed Oct. 26, 1993, which is a continuation-in-part of U.S. application No. 07/981,627, filed Nov. 25, 1992, now abandoned.

FIELD OF THE INVENTION

The present invention concerns monoepoxide compounds, monothiirane compounds, epoxy resins, polythiirane resins and vinyl ester resins which contain one or more discotic mesogenic moieties, as well as thermosettable compositions containing one or more of said resins and products resulting from thermosetting (curing) said curable compositions.

BACKGROUND OF THE INVENTION

A molecule composed of a disk-shaped, rigid, essentially planar core to which four or more flexible aliphatic chains or tails are attached forms the basic structure inherent to the discotic mesogen. This disk-like anisotropy of molecular shape leads to the discotic mesophase wherein the disk-like molecules organize together into thermotropic liquid crystalline columnar structures. By way of contrast, the more commonly encountered rodlike anisotropy of molecular shape, does not lead to the discotic mesophase. According to S. Chandrasekhar and G. S. Ranganath, *Rep. Prog. Phys.*, 53(1), 57 (1989), discotic liquid crystallinity is generally classified into two structural categories: "The columnar phase, in its simplest form, has long-range translational periodicity in two dimensions and liquid-like disorder in the third, whereas the nematic phase is an orientationally ordered arrangement of discs without any long-range translational order." The discotic nematic phase contrasts to the nematic phase exhibited by numerous rodlike mesogenic molecules in that the director represents the preferred orientation of the short molecular axis versus the long molecular axis for rodlike mesogenic molecules. Some variation on the flat, planar core structure of the discotic mesogen can be tolerated while still preserving the columnar mesophase. For example, G. Cometti, E. Dalcanale and A. Du Vosel, *Liquid Crystals*, 11(1), 93–100 (1992) have prepared bowl-shaped molecules which exhibit a columnar liquid crystalline phase. Similarly, J. Malthete and A. Collet, *Nouve. J. Chem.*, 9, 151 (1985) have replaced the flat, planar core structure with a conical one providing molecules which still exhibit a columnar mesophase. The presence of the flexible aliphatic chains or tails attached to the disk-shaped core is critical to achieving the discotic liquid crystalline state. Chemical structure, length and presence of branching are some of the variables relating to the aliphatic chains that are frequently manipulated to modify discotic mesophase structure and behavior. Regarding the number of flexible aliphatic chains that are required to achieve the discotic liquid crystalline state, it is fully recognized that certain exceptional molecules exist, such as the 1,7,13-trialkanoyldecacyclenes prepared and characterized by E. Keinan, S. Kumar, R. Moshenberg, R. Ghirlando and E. Wachtel, *Adv. Mater.*, 3, 251 (1991) and the 1,3,5-tri(4-alkoxyphenoxycarbonyl)benzenes (the hexyloxy and decyloxy homologs) prepared and characterized by S. Takenaka, K. Nishimura and S. Kusabayashi, *Mol. Cryst. Liq. Cryst.*, 111, 227–236 (1984). Thus the discotic liquid crystalline state depends upon the intermolecular attraction between the disk-like core structures leading to molecular stacking coupled with hydrophobic interaction between aliphatic chains which precludes long range three dimensional order. Thus for the 1,7,13-trialkanoyldecacyclenes the presence of the large polycyclic aromatic core maximizes attractive core to core interactions and thus appears to reduce the requirement for hydrophobic interaction between the aliphatic chains required for the discotic mesophase to be achieved. For the 1,3,5-tri(4-alkoxyphenoxycarbonyl) benzenes (the hexyloxy and decyloxy homologs), interaction of the 4-alkoxyphenoxycarbonyl groups induces molecular symmetry as determined by conformational isomerization around the ester plus increased polarizability due to the alkoxy groups and thus appears to reduce intermolecular attraction between the disk-like core structures required for the discotic mesophase to be achieved.

For molecules such as triglycidyloxynaphthalenes, specifically, 1,3,6-triglycidyloxynaphthalene, disclosed in Japanese Patent No. 1-268,715-A; the triglycidyl ether of trihydroxybiphenyl, tetraglycidylbenzophenone, and the tetraglycidyl ether of bisresorcinol, disclosed in U.S. Pat. No. 5,037,934; 1,3,5-triglycidyloxybenzene, disclosed in U.S. Pat. No. 4,992,488; 3,3',5-triglycidyloxybiphenyl disclosed in U.S. Pat. No. 4,954,583; the diglycidyl ethers of tetra-$C_{1-12}$ hydrocarbyl group substituted dihydroxybenzenes, disclosed in WO 86/03507; the diglycidyl ethers of tetra-$C_{1-10}$ hydrocarbyl or hydrocarbyloxy group substituted dihydroxybenzenes, disclosed in U.S. Pat. No. 5,164,464; or the monoepoxyhexahydrobenzyl (mono-, di-, or triglycidyloxy substituted)benzoates disclosed in SU 591,471 discotic liquid crystallinity is not reported nor expected. In the relationship between the core to core interactions and the hydrophobic interaction between the aliphatic chains required for the discotic mesophase to be achieved, a certain minimum constraint in the size and other variables of the aromatic core and in the number, structure (size, type, etc.) of aliphatic chains exists. Thus, the benzene, naphthalene, biphenyl or benzophenone groups of the aforementioned compounds possess inadequate core to core attractive interactions in combination with inadequate hydrophobic interactions between the aliphatic chains (glycidyl groups, hydrocarbyl groups, etc.) substituted therein to be discotic mesogens.

Diglycidyl ethers of bis(anthrols) and bis(naphthols) of the following formulas are known from U.S. Pat. No. 4,908,424:

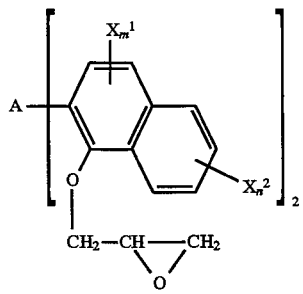

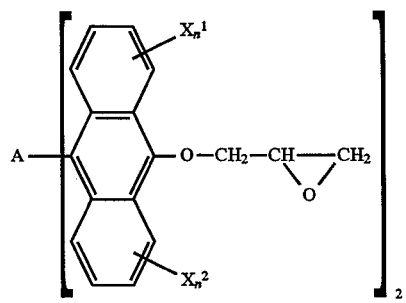

wherein each $X^1$ and $X^2$ is independently an alkyl group containing 1 to 4 carbon atoms or a halogen atom having an atomic number of from 9 to 35, inclusive; m is 0, 1 or 2; n is 0, 1, 2, 3 or 4; and A is a divalent hydrocarbon radical selected from the group consisting of and alkylene group containing from 3 to 8 carbon atoms, or a radical derived from a non-aromatic carbocyclic group or a dialkyl aromatic or non-aromatic carbocyclic group containing from 7 to 24 carbon atoms in which each alkyl group contains from 1 to 8 carbon atoms and the carbocyclic group comprises a central non-aromatic ring containing 5 to 7 carbon atoms in a ring or a central aromatic carbocyclic ring, each central ring optionally bridged or fused with a non-aromatic or aromatic carbocyclic ring. When A is a dialkyl aromatic or non-aromatic carbocyclic group, it should be understood that the bonds from A to the anthrol or naphthol group are from the alkyl substitutents of the dialkyl carbocyclic group. Discotic liquid crystallinity is not reported nor expected for these compounds. Specifically, diglycidyl α,α'-bis(10-anthr-9-one)-p-diisopropylbenzene with a melting point of 160–170 deg. C. and the diglycidyl ether of α,α'-bis(1-hydroxy-2-naphthyl)-p-diisopropylbenzene with a melting point of 167–168 deg. C. were prepared and polymerized with a variety of phenolic and amine curing agents. Discotic liquid crystallinity is not reported for either of these compounds nor the polymerized compositions thereof.

Liquid crystalline polymers containing disk-like mesogens both in the main chain of the polymer backbone and as side chains have been prepared. For example, W. Kreuder and H. Ringsdorf, *Makromol. Chem., Rapid Commun.*, 4, 807–815 (1983) prepared discotic polysiloxanes containing pentaalkyloxysubstituted triphenylene moieties attached as side chains to the polymer backbone via flexible spacers. Similarly, W. Kreuder, H. Ringsdorf and P. Tschirner, *Makromol. Chem., Rapid Commun.*, 6, 367–373 (1985) prepared discotic polyesters containing tetraalkyloxysubstituted triphenylene moieties incorporated into the main chains of the polymer backbone. Both classes of polymers exhibited discotic liquid crystalline behavior. Virtually all of the discotic liquid crystalline polymers known to date are thermoplastic.

The present invention provides the heretofore unknown classes of thermosettable epoxy, polythiirane and vinyl ester resin compositions containing one or more discotic mesogenic moieties. Said resins exhibit unique molecular order in the melt phase as a result of the discotic mesogenic moieties contained therein. Surprisingly, in certain compositions of the present invention, the flexible aliphatic chains or tails required for discotic liquid crystallinity can be completely replaced by thermosettable glycidyl ether moieties, while still maintaining discotic liquid crystallinity. The discotic liquid crystalline morphology can result in enhanced physical and mechanical properties, such as, for example, increased strength and thermal stability.

The term "discotic mesogenic moiety" or "discotic mesogen" is used herein to describe a molecule composed of a disk-shaped, rigid, essentially planar core to which flexible aliphatic chains or tails may be attached. Said flexible aliphatic chains or tails are attached via functional groups present in the discotic mesogenic moiety. Furthermore, the vicinal epoxide group, the vicinal thiirane group and the vinyl ester (prepared via reaction of the epoxide group and a polymerizable ethylenically monounsaturated monocarboxylic acid) group are all considered as members of the group of flexible aliphatic chains or tails.

SUMMARY OF THE INVENTION

One aspect of the present invention concerns compounds containing only one vicinal epoxide group per molecule and at least one discotic mesogenic moiety per molecule.

Another aspect of the present invention concerns compounds containing only one vicinal thiirane group per molecule and at least one discotic mesogenic moiety per molecule.

Another aspect of the present invention pertains to an epoxy resin containing an average of more than one vicinal epoxide group per molecule characterized by containing at least one discotic mesogenic moiety per molecule, with the proviso that said epoxy resin is not an epoxy resin represented by the formula

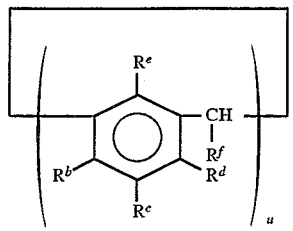

where $R^b$ and $R^d$ are either the same or difference and are selected from hydrogen, hydroxyl, alkoxy, alkenyloxy and epoxypropyloxy (glycidyloxy); $R^c$ is selected form hydrogen, halogen, alkenyl, alkyl optionally substituted with halogen, arylalkyl optionally substituted with halogen, and aryl optional substituted with halogen; $R^f$ is selected from hydrogen, alkyl optionally substituted with halogen, arylalkyl optionally substituted with halogen and aryl optionally substituted with alkyl or halogen or both; Re is selected from hydrogen, halogen, alkyl or alkenyl; u is an integer from 3 to 10; and with the proviso that at least one epoxypropyloxy (glycidyloxy) group per molecule is present.

Another aspect of the present invention concerns epoxy resins containing an average of more than one vicinal epoxide group per molecule and at least one discotic mesogenic moiety per molecule, with the proviso that said epoxy resin can not be an epoxy resin of the formula

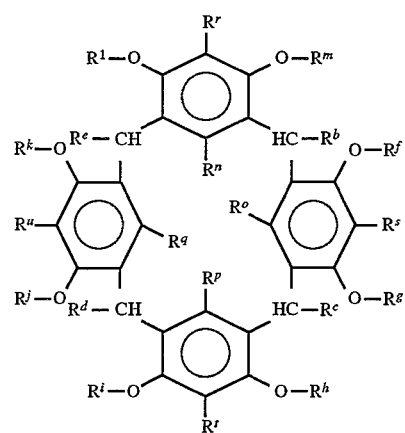

in which $R^b$, $R^c$, $R^d$, $R^e$, are the same of different, but preferably the same, and each is hydrogen or $C_1$–$C_{12}$ alkyl; $R^f$, $R^g$, $R^h$, $R^i$, $R^j$, $R^k$, $R^l$, $R^m$ are the same or different, and each is $C_1$–$C_{12}$ alkyl or alkenyl or the glycidyl residue,

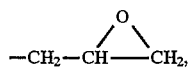

such that at least two such groups are glycidyl residues; and $R^n$, $R^o$, $R^p$, $R^q$, $R^r$, $R^s$, $R^t$, $R^u$ are the same or different and are hydrogen, halogen, or $C_1$–$C_{12}$ alkyl or alkenyl.

Another aspect of the present invention concerns polythiirane resins containing an average of more than one vicinal thiirane group per molecule and at least one discotic mesogenic moiety per molecule.

Another aspect of the present invention concerns a composition comprising (A) at least one of (1) at least one compound containing only one vicinal epoxide group per molecule and at least one discotic mesogenic moiety per molecule; or (2) at least one compound containing only one vicinal thiirane group per molecule and at least one discotic mesogenic moiety per molecule; or (3) any combination of (1) and (2); with (B) at least one of (1) at least one epoxy resin containing an average of more than one vicinal epoxide group per molecule and at least one discotic mesogenic moiety per molecule; or (2) at least one polythiirane resin containing an average of more than one vicinal thiirane group per molecule and at least one discotic mesogenic moiety per molecule; or (3) any combination of (1) and (2).

Another aspect of the present invention concerns a composition comprising (A) at least one of (1) at least one epoxy resin containing an average of more than one vicinal epoxide group per molecule and at least one discotic mesogenic moiety per molecule; or (2) at least one polythiirane resin containing an average of more than one vicinal thiirane group per molecule and at least one discotic mesogenic moiety per molecule; or (3) any combination of (1) and (2);

(B) at least one of (1) at least one epoxy resin containing an average of more than one vicinal epoxide group per molecule and which does not contain any discotic mesogenic moieties; or (2) at least one polythiirane resin containing an average of more than one vicinal thiirane group per molecule and which does not contain any discotic mesogenic moieties; or (3) any combination of (1) and (2); and (C) optionally, at least one of (1) at least one compound containing only one vicinal epoxide group per molecule and at least one discotic mesogenic moiety per molecule; or (2) at least one compound containing only one vicinal thiirane group per molecule and at least one discotic mesogenic moiety per molecule; or (3) at least one compound containing only one vicinal epoxide group per molecule and which does not contain any discotic mesogenic moieties; or (4) at least one compound containing only one vicinal thiirane group per molecule and which does not contain any discotic mesogenic moieties; or (5) any combination of (1), (2), (3) or (4), with the proviso that said epoxy resin of (A1) can not be an epoxy resin of the formula

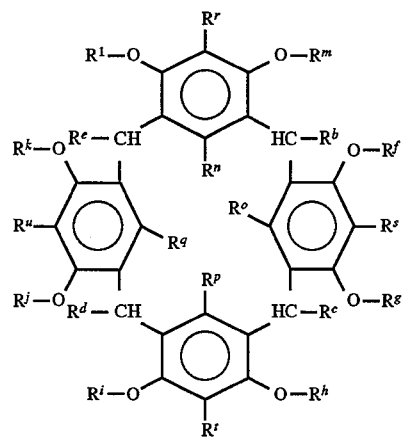

in which $R^b$, $R^c$, $R^d$, $R^e$, are the same of different, but preferably the same, and each is hydrogen or $C_1$–$C_{12}$ alkyl; $R^f$, $R^g$, $R^h$, $R^i$, $R^j$, $R^k$, $R^l$, $R^m$ are the same or different, and each is $C_1$–$C_{12}$ alkyl or alkenyl or the glycidyl residue,

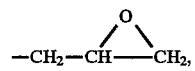

such that at least two such groups are glycidyl residues; and $R^n$, $R^o$, $R^p$, $R^q$, $R^r$, $R^s$, $R^t$, $R^u$ are the same or different and are hydrogen, halogen, or $C_1$–$C_{12}$ alkyl or alkenyl, if only components (A1) and (B1) are present.

Another aspect of the present invention concerns a polymerizable composition comprising (A) at least one of (1) at least one compound containing only one vicinal epoxide group per molecule and at least one discotic mesogenic moiety per molecule; or (2) at least one compound containing only one vicinal thiirane group per molecule and at least one discotic mesogenic moiety per molecule; or (3) any combination of (1) and (2);

(B) at least one initiator therefor; and (C) at least one catalyst selected from Lewis acids or protic acids or any combination thereof.

Another aspect of the present invention concerns a curable composition comprising (A) at least one of (1) at least one epoxy resin containing an average of more than one vicinal epoxide group per molecule and at least one discotic mesogenic moiety per molecule; or (2) at least one polythiirane resin containing an average of more than one vicinal thiirane group per molecule and at least one discotic mesogenic moiety per molecule; or (3) any combination of (1) and (2); and (B) a curing amount of at least one suitable curing agent or curing catalyst therefor or a combination of curing agents and curing catalysts, with the proviso that said epoxy resin of (A1) can not be an epoxy resin of the formula

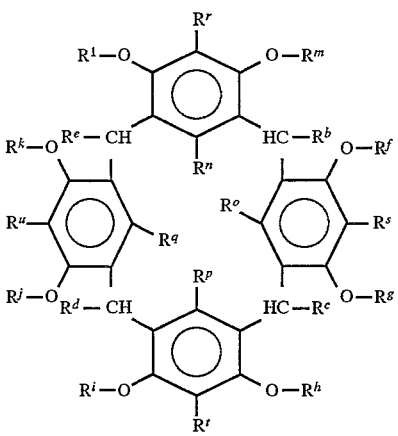

in which $R^b$, $R^c$, $R^d$, $R^e$, are the same of different, but preferably the same, and each is hydrogen or $C_1$–$C_{12}$ alkyl; $R^f$, $R^g$, $R^h$, $R^i$, $R^j$, $R^k$, $R^l$, $R^m$ are the same or different, and each is $C_1$–$C_{12}$ alkyl or alkenyl or the glycidyl residue,

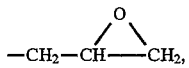

such that at least two such groups are glycidyl residues; and $R^n$, $R^o$, $R^p$, $R^q$, $R^r$, $R^s$, $R^t$, $R^u$ are the same or different and are hydrogen, halogen, or $C_1$–$C_{12}$ alkyl or alkenyl, if only components (A1) and (B) are present.

Another aspect of the present invention concerns a curable composition comprising (A) a blend comprising
  (1) at least one of
    (a) at least one compound containing only one vicinal epoxide group per molecule and at least one discotic mesogenic moiety per molecule; or
    (b) at least one compound containing only one vicinal thiirane group per molecule and at least one discotic mesogenic moiety per molecule; or
    (c) at least one compound containing only one vicinal epoxide group per molecule and which does not contain any discotic mesogenic moieties; or
    (d) at least one compound containing only one vicinal thiirane group per molecule and which does not contain any discotic mesogenic moieties; or
    (e) any combination of (a), (b), (c) or (d); and
  (2) at least one of
    (a) at least one epoxy resin containing an average of more than one vicinal epoxide group per molecule and at least one discotic mesogenic moiety per molecule; or
    (b) at least one polythiirane resin containing an average of more than one vicinal thiirane group per molecule and at least one discotic mesogenic moiety per molecule; or
    (c) any combination of (a) and (b); and (B) a curing amount of at least one suitable curing agent or curing catalyst therefor or a combination of curing agents and curing catalysts.

Another aspect of the present invention concerns a curable composition comprising (A) a blend comprising
  (1) at least one of
    (a) at least one epoxy resin containing an average of more than one vicinal epoxide group per molecule and at least one discotic mesogenic moiety per molecule; or
    (b) at least one polythiirane resin containing an average of more than one vicinal thiirane group per molecule and at least one discotic mesogenic moiety per molecule; or
    (c) any combination of (a) and (b);
  (2) at least one of
    (a) at least one epoxy resin containing an average of more than one vicinal epoxide group per molecule and which does not contain any discotic mesogenic moieties; or
    (b) at least one polythiirane resin containing an average of more than one vicinal thiirane group per molecule and which does not contain any discotic mesogenic moieties; or
    (c) any combination of (a) and (b); and
  (3) optionally, at least one of
    (a) at least one compound containing only one vicinal epoxide group per molecule and at least one discotic mesogenic moiety per molecule; or
    (b) at least one compound containing only one vicinal thiirane group per molecule and at least one discotic mesogenic moiety per molecule; or
    (c) at least one compound containing only one vicinal epoxide group per molecule and which does not contain any discotic mesogenic moieties; or
    (d) at least one compound containing only one vicinal thiirane group per molecule and which does not contain any discotic mesogenic moieties; or
    (e) any combination of (a), (b), (c) or (d); with (B) a curing amount of at least one suitable curing agent or curing catalyst therefor or a combination of a curing agent and a curing catalyst, with the proviso that said epoxy resin of (A1a) can not be an epoxy resin of the formula

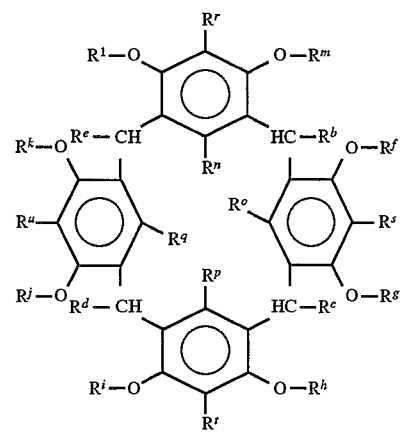

in which $R^b$, $R^c$, $R^d$, $R^e$, are the same of different, but preferably the same, and each is hydrogen or $C_1$–$C_{12}$ alkyl; $R^f$, $R^g$, $R^h$, $R^i$, $R^j$, $R^k$, $R^l$, $R^m$ are the same or different, and each is $C_1$–$C_{12}$ alkyl or alkenyl or the glycidyl residue,

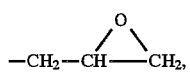

such that at least two such groups are glycidyl residues; and $R^n$, $R^o$, $R^p$, $R^q$, $R^r$, $R^s$, $R^t$, $R^u$ are the same or different and are hydrogen, halogen, or $C_1$–$C_{12}$ alkyl or alkenyl, if only components (A1a), (A2a) and (B) are present.

Another aspect of the present invention concerns vinyl ester resins containing at least one discotic mesogenic moiety per molecule which are prepared by reacting (A) at least one epoxy resin containing an average of more than one vicinal epoxide group per molecule and at least one discotic mesogenic moiety per molecule; and
(B) optionally, at least one of
  (a) at least one compound containing only one vicinal epoxide group per molecule and at least one discotic mesogenic moiety per molecule; or
  (b) at least one compound containing only one vicinal epoxide group per molecule and which does not contain any discotic mesogenic moieties; or
  (c) at least one compound containing one vicinal epoxide group per molecule and which does not contain any discotic mesogenic moieties; or
  (d) any combination of (a), (b), or (c); with
(C) one or more polymerizable ethylenically monounsaturated monocarboxylic acids.

Another aspect of the invention concerns a curable composition comprising
(A) one or more vinyl ester resins containing at least one discotic mesogenic moiety per molecule; and
(B) one or more free radical forming catalysts, or one or more accelerating agents therefor or a combination of free radical forming catalysts and accelerating agents.

Another aspect of the invention concerns a curable composition comprising
(A) one or more-vinyl ester resins containing at least one discotic mesogenic moiety per molecule; and
(B) one or more polymerizable ethylenically unsaturated monomers; and
(C) optionally, one or more free radical forming catalysts or accelerating agents therefor or a combination of free radical forming catalysts and accelerating agents.

Another aspect of the present invention concerns the product or article resulting from polymerizing the aforementioned polymerizable compositions.

Another aspect of the present invention concerns the product or article resulting from curing the aforementioned curable compositions.

Another aspect of the present invention concerns the product or article resulting from curing the aforementioned curable compositions wherein said curable composition is oriented either prior to or during or both prior to and during curing.

Another aspect of the present invention concerns the product or article resulting from polymerizing the aforementioned polymerizable compositions wherein said polymerizable compositions are oriented either prior to or during or both prior to and during polymerization.

Each of the above mentioned compositions can either "comprise", "consist essentially of" or "consist of" the individual components specifically enumerated therein.

DETAILED DESCRIPTION OF THE INVENTION

DISCOTIC MESOGEN-CONTAINING COMPOUNDS

Typical of the discotic mesogen-containing compounds used to prepare the monoepoxide compounds or epoxy resins which contain one or more discotic moieties of the present invention are those represented by the Formulas I, II, III, IV, V and VI Formula I $Z_p$—D Formula II $Z_p^1$—D—[($Q_n$—$R^1$)$_m^1$—$Q_n$—R]$_m$ Formula III D—[($Q_n$—$R^1$)$_m^1$—$Q_n$—Ar—Z]$_p$ Formula IV $Z_p^1$—D—[($Q_n$—$R^1$)$_m^1$—$Q_n$—Ar—Z]$_m$ Formula V D—[($Q_n$—$R^1$)$_m^1$—($Q_n$—Ar)$_n$—$Q_n$—$Z^1$]$_p$ Formula VI ($Z^1$—$Q_n$)$_p^1$—D—[($Q_n$—$R^1$)$_m^1$—$Q_n$—R]$_m$ wherein each Ar is a benzene, naphthalene or biphenyl moiety having from 6 to about 12 carbon atoms; D is a disk-shaped core selected from the group consisting of, triphenylenes, azatriphenylenes, hexa(4-substituted benzoates) of triphenylene, alkyl or substituted alkyl pentakis(phenylethynyl)phenyl ethers, multi((phenyl) alkynyl)triphenylenes, hexakis((phenyl)alkynyl)benzenes, hexakis((phenyl)alkynyl)naphthalenes, hexa(4-substituted benzoates) of benzene, hexakis(aryloxy)benzenes, truxenes, trithiatruxenes, trioxatruxenes, triazatruxenes, triketotruxenes, phthalocyanines, metallophthalocyanines, porphyrins, metalloporphyrins, macrocyclic polyamines, cyclomultibenzylenes, metacyclophanes, anthraquinones, tricycloquinazoline, bipyranylidenes, triptycenes, bis[1,2-bis(phenyl)ethane-1,2-dithiolato]metals, bis(5-diketonato) metal complexes, triaryl pyrylium salts, decacyclenes, dibenzopyrenes, tungsten-oxocalix[4]arenes and cis,cis-(3, 5-dihydroxycyclohexyl)-3,4,5-tri(substituted)benzoates; each Q is independently a —O—CO—, —CO—O—, —CO—$NR^1$—, —$NR^1$—CO—, —S—CO—, —CO—S—, —O—CO—O—, —$NR^1$—CO—$NR^1$—, —$NR^1$—CO—O—, —O—CO—$NR^1$—, —O—, —S—, —S—S—, —$SO^2$—, or —CO— group; R is a monovalent hydrocarbyl group having from 1 to about 20 carbon atoms; $R^1$ is a divalent hydrocarbyl group having from 1 to about 20 carbon atoms; $R^2$ is —H or a monovalent hydrocarbyl group having from one to about 12 carbon atoms; each $R^a$ is independently hydrogen or an alkyl or haloalkyl group with the proviso that only one $R^a$ group can be a haloalkyl group; each Z is independently a —OH, —SH, —CO—OH, —$NHR^2$, —O—(CHR$^a$—CHR$^a$—O—)$_p^2$—CHR$^a$—CHR$^a$—OH, —CO—O—(CHR$^a$—CHR$^a$—O—)$_p^2$—CHR$^a$—CHR$^a$—OH, —S—(CHR$^a$—CHR$^a$—O—)$_p^2$—CHR$^a$—CHR$^a$—OH, —NR—(CHR$^a$—CHR$^a$—O—)$_p^2$—CHR$^a$—CHR$^a$—OH, or —N—((CHR$^a$—CHR$^a$—O—)$_p^2$—CHR$^a$—CHR$^a$—OH)$_2$, group; each $Z^1$ is independently an epoxidizable ethylenically unsaturated group having from 2 to about 20, preferably from about 10 to about 2, more preferably from about 4 to about 2 carbon atoms; m has a value from 1 to about 20, preferably from about 1 to about 10, more preferably from about 2 to about 6; $m^1$ has a value from zero to about 5; n has a value of zero or 1; p has a value from 3 to about 20, preferably from 3 to about 10, more preferably from 3 to about 8; $p^1$ has a value from 1 to about 20, preferably from about 1 to about 10, more preferably from about 2 to about 6; $p^2$ has a value of zero to about 99, preferably from about zero to about 50, more preferably from about zero to about 10; with the proviso that the sum of $p^1$ and m in Formulas II, IV, or VI must have a value of at least 3 or more.

The term hydrocarbyl as employed herein means any aliphatic, cycloaliphatic, aromatic, aryl substituted aliphatic or cycloaliphatic, or aliphatic or cycloaliphatic substituted aromatic groups. The aliphatic or cycloaliphatic groups can be saturated or unsaturated. Likewise, the term hydrocarbyloxy means a hydrocarbyl group having an oxygen linkage between it and the carbon atom to which it is attached.

Representative discotic mesogen-containing compounds used to prepare the monoepoxide compounds and epoxy resins containing at least one discotic moiety per molecule of the present invention include, for example, the hexakis (substituted)benzenes, such as 1,2,3,4,5,6-hexahydroxybenzene, 1,2,3,4,5,6-hexacarboxybenzene, 1,2,3,4,5,6-hexamercaptobenzene, 1,2,3,4,5,6-hexa-N-methylaminobenzene; the triphenylenes, such as 2,3,6,7,10,11-hexahydroxytriphenylene, 2,3,6,7,10,11-hexacarboxytriphenylene, 2,3,6,7,10,11-hexamercaptotriphenylene, 2,6,10-trihydroxy-3,7,11-trimethoxytriphenylene, 2,6,10-trimethoxy-3,7,11-trihydroxytriphenylene, 2-hydroxy-3,6,7,10,11-pentamethoxytriphenylene, 2-methoxy-3,6,7,10,11-pentahydroxytriphenylene, 2,6,10-trihydroxy-3,7,11-tridodecyloxytriphenylene, 2,6,10-trihydroxytriphenylene, 3,7,11-trihydroxytriphenylene, 2,6,10-trihydroxy-3,6,7-trimethyltriphenylene, 3,7,11-trihydroxy-2,6,10-trimethyltriphenylene, 3,6,7,11-tetrahydroxy-2,10-triphenylenediacetate, 3,6,10,11-tetrahydroxy-2,7-triphenylenediacetate, 3,6,7,10-tetrahydroxy-2,11-triphenylenediacetate, 3,6,7,11-tetrahydroxy-2,10-triphenylenedistearate, 3,6,7,11-tetracarboxy-2,10-triphenylenediacetate, 2,3,6,7,10,11-tris(N,N'-ethylenediamino)triphenylene, 2,3,6,7,10,11-tris(N-methyl, N'-ethylenediamino)triphenylene, 1,5,9-trihexyl-2,3,6,7,10,11-tris(N,N'-ethylenediamino) triphenylene; the azatriphenylenes, such as 2,3,6,7,10,11-hexahydroxy-1,5,9-triazatriphenylene, 2,3,6,7,10,11-hexacarboxy-1,5,9-triazatriphenylene, 2,6,10-trihydroxy-1,5,9-triazatriphenylene, 2,6,10-trihydroxy-3,7,11-trihexyl-1,5,9-triazatriphenylene, 2-hydroxy-3,6,7,10,11-pentamethoxy-1,5,9-triazatriphenylene, 3,7,11-trihydroxy-2,6,10-triazatriphenylene, 2,6,10-trihydroxy-3,7,11-triazatriphenylene, 2,3,6,7,10,11-hexahydroxy-1,4,5,8,9,12-hexaazatriphenylene, 2,3,6,7,10,11-hexacarboxy-1,4,5,8,9,12-hexaazatriphenylene; the multi(phenyl) alkynyltriphenylenes, such as 2,3,6,7,10,11-hexakis((4-hydroxyphenyl)ethynyltriphenylene, 2,6,10-tris((4-hydroxyphenyl)ethynyltriphenylene, 3,7,11-trimethoxy-2,6,10-tris((4-hydroxyphenyl)ethynyltriphenylene; the alkyl or substituted alkyl pentakis(phenylethynyl)phenyl ethers, such as 11-(pentakis((4-hydroxyphenyl)ethynyl)phenoxy) undecane, 11-(pentakis((4-hydroxyphenyl)ethynyl) phenoxy)undecanoic acid ethyl ester; the hexakis((phenyl) alkynyl)benzenes and the hexakis((phenyl)alkynyl) naphthalenes, such as hexakis((4-hydroxyphenyl)ethynyl) benzene,hexakis((3,5-dimethyl-4-hydroxyphenyl)ethynyl) benzene, 1,2,3,5,7-hexakis((4-hydroxyphenyl)ethynyl) naphthalene; the hexakis(aryloxy)benzenes such as hexakis (4-hydroxyphenyloxy)benzene, hexakis(3,5-dimethyl-4-hydroxyphenyloxy)benzene; the truxenes such as 2,3,7,8,12,13-hexahydroxytruxene, 2,3,7,8,12,13-hexamercaptotruxene, 2,3,7,8,12,13-hexacarboxytruxene, 2,3,7,8,12,13-hexa-N-methylaminotruxene, 2,7,12-trihydroxytruxene, 3,8,13-trihydroxytruxene, 2,7,12-trihydroxy-3,8,13-trimethyltruxene, 2,7,12-trihydroxy-3,8,13-triacetoxytruxene, 2,7,12-trimethyl-3,8,13-trihydroxytruxene, 2-hydroxy-3,7,8,12,13-pentamethyltruxene, 2,8-dihydroxy-3,7,12,13-tetramethyltruxene, 1,6,11-trimethyl-3,8,13-trihydroxytruxene; the trithiatruxenes such as 2,3,7,8,12,13-hexahydroxy(1,2-b; 3,4-b'; 5,6-b")trisbenzothiophene, 2,3,7,8,12,13-hexacarboxy(1,2-b; 3,4-b'; 5,6-b") trisbenzothiophene, 2,3,7,8,12,13-hexamercapto(1,2-b; 3,4-b'; 5,6-b")trisbenzothiophene, 2,3,7,8,12,13-hexa-N-methylamino(1,2-b; 3,4-b'; 5,6-b")trisbenzothiophene, 2,7,12-trihydroxy(1,2-b; 3,4-b'; 5,6-b")trisbenzothiophene, 3,8,13-trihydroxy(1,2-b; 3,4-b'; 5,6-b")trisbenzothiophene, 2,7,12-trihexyloxy-3,8,13-trihydroxy(1,2-b; 3,4-b'; 5,6-b") trisbenzothiophene, 2,7,12-trihexyl-3,8,13-trihydroxy(1,2-b; 3,4-b'; 5,6-b")trisbenzothiophene, 3,7,8,12,13-pentamethyl-2-hydroxy(1,2-b; 3,4-b'; 5,6-b") trisbenzothiophene, 3,7,12,13-tetramethyl-2,8-dihydroxy(1,2-b; 3,4-b'; 5,6-b")trisbenzothiophene; the trioxatruxenes such as 2,3,7,8,12,13-hexahydroxy(1,2-b; 3,4-b'; 5,6-b") trisbenzofuran, 2,3,7,8,12,13-hexacarboxy(1,2-b; 3,4-b'; 5,6-b")trisbenzofuran, 2,3,7,8,12,13-hexamercapto(1,2-b; 3,4-b'; 5,6-b")trisbenzofuran, 2,3,7,8,12,13-hexa-N-methylamino(1,2-b; 3,4-b'; 5,6-b")trisbenzofuran, 2,7,12-trihydroxy(1,2-b; 3,4-b'; 5,6-b")trisbenzofuran, 3,8,13-trihydroxy(1,2-b; 3,4-b'; 5,6-b")trisbenzofuran, 2,7,12-trihexyloxy-3,8,13trihydroxy(1,2-b; 3,4-b'; 5,6-b") trisbenzofuran, 2,7,12-trihexyl-3,8,13-trihydroxy(1,2-b; 3,4-b'; 5,6-b")trisbenzofuran, 3,7,8,12,13-pentamethyl-2-hydroxy(1,2-b; 3,4-b'; 5,6-b")trisbenzofuran, 3,7,12,13-tetramethyl-2,8-dihydroxy(1,2-b; 3,4-b'; 5,6-b") trisbenzofuran; the triazatruxenes such as 2,3,7,8,12,13-hexahydroxy(1,2-b; 3,4-b'; 5,6-b")trisbenzo-N-methylpyrrole, 2,3,7,8,12,13-hexahydroxy(1,2-b; 3,4-b'; 5,6-b")trisbenzo-N-ethylpyrrole, 2,3,7,8,12,13-hexacarboxy (1,2-b; 3,4-b'; 5,6-b")trisbenzo-N-methylpyrrole, 2,3,7,8,12,13-hexamercapto(1,2-b; 3,4-b'; 5,6-b")trisbenzo-N-methylpyrrole, 2,3,7,8,12,13-hexa-N-methylamino(1,2-b; 3,4-b'; 5,6-b")trisbenzo-N-methylpyrrole, 2,7,12-trihydroxy (1,2-b; 3,4-b'; 5,6-b")trisbenzo-N-methylpyrrole, 3,8,13-trihydroxy(1,2-b; 3,4-b'; 5,6-b")trisbenzo-N-methylpyrrole, 2,7,12-trihexyloxy-3,8,13-trihydroxy(1,2-b; 3,4-b'; 5,6-b") trisbenzo-N-methylpyrrole, 2,7,12-trihexyl-3,8,13-trihydroxy(1,2-b; 3,4-b'; 5,6-b")trisbenzo-N-methylpyrrole, 3,7,8,12,13-pentamethyl-2-hydroxy(1,2-b; 3,4-b'; 5,6-b") trisbenzo-N-methylpyrrole, 3,7,12,13-tetramethyl-2,8-dihydroxy(1,2-b; 3,4-b'; 5,6-b")trisbenzo-N-methylpyrrole; the triketotruxenes such as those represented by the formulas

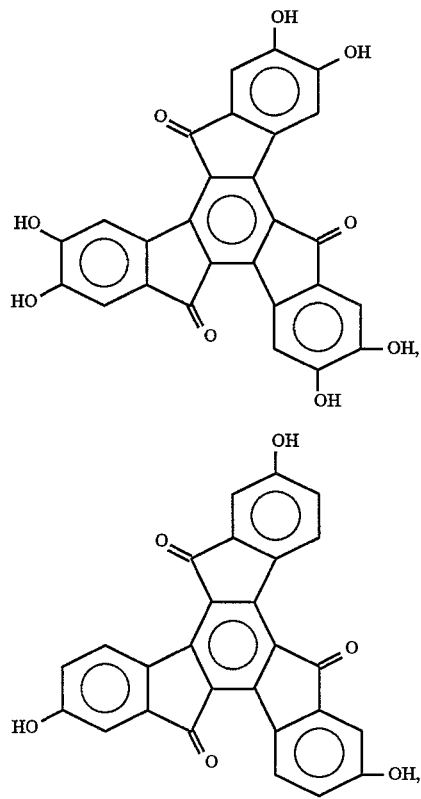

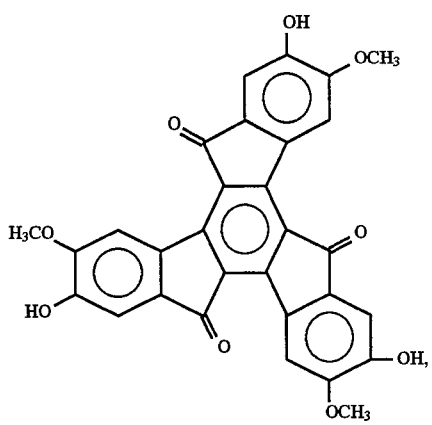
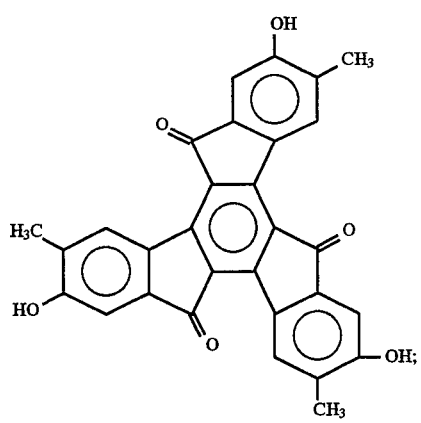
the phthalocyanines, metallophthalocyanines, porphyrins and metalloporphyrins such as those represented by the formulas
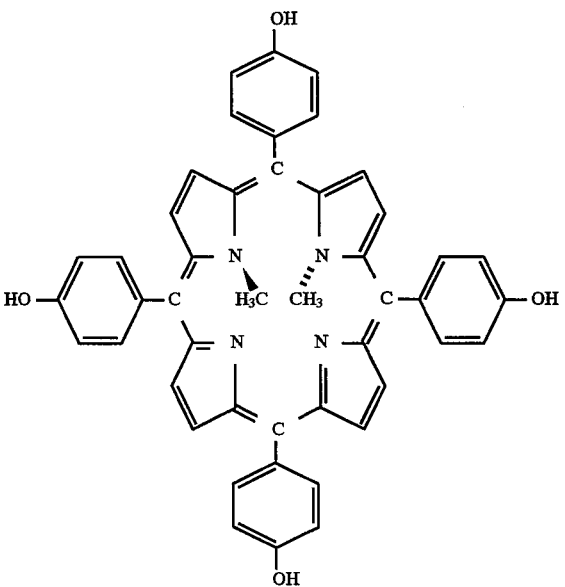

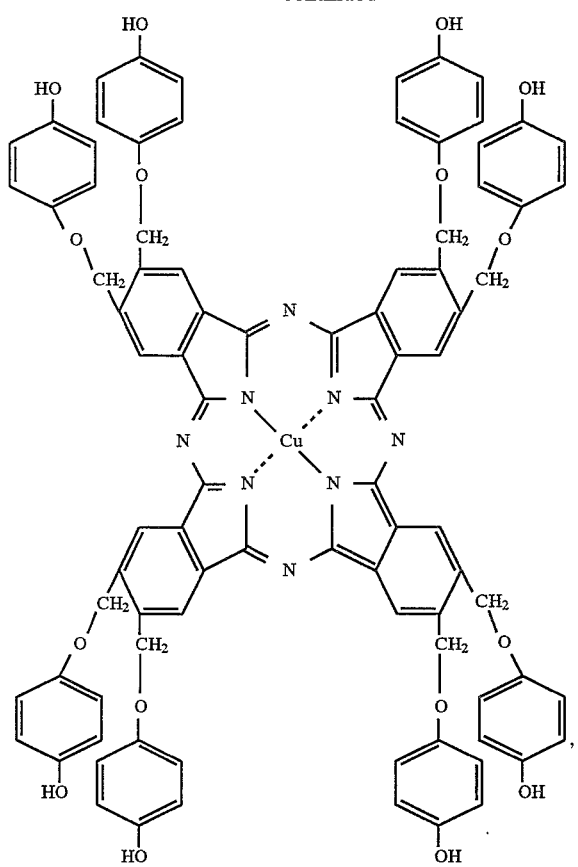
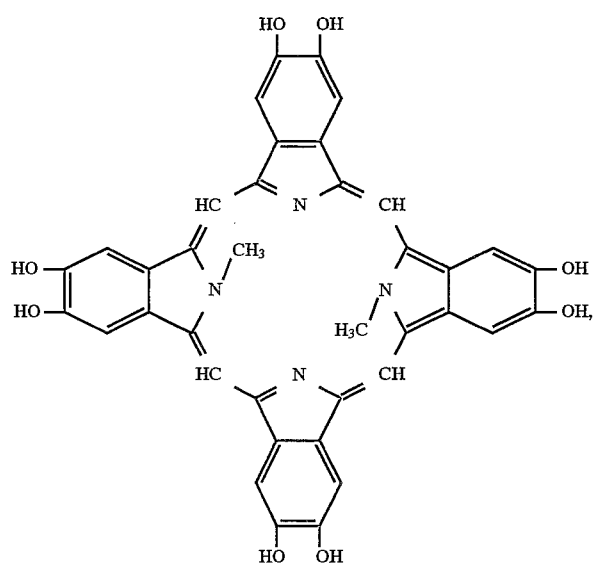

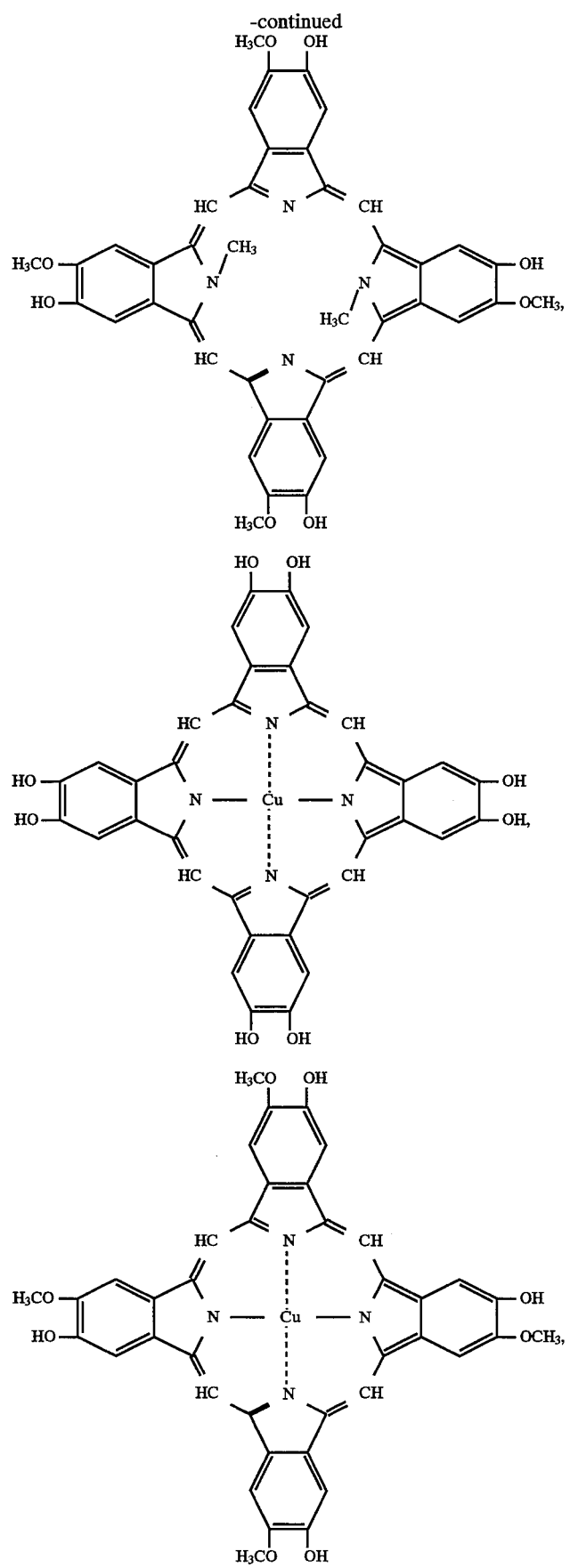

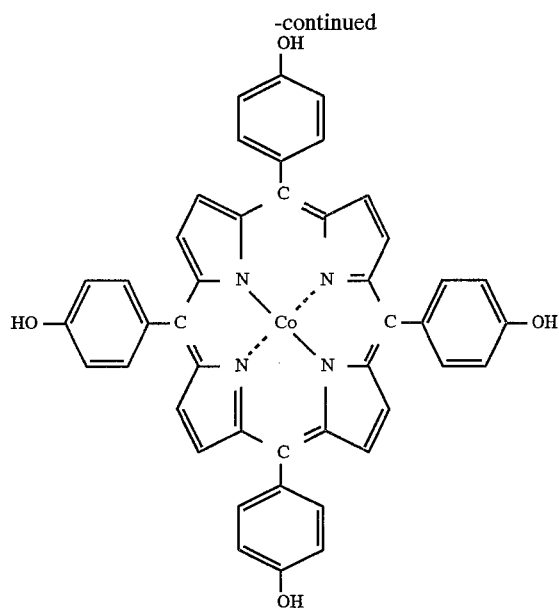
the macrocyclic polyamines such as those represented by the formulas
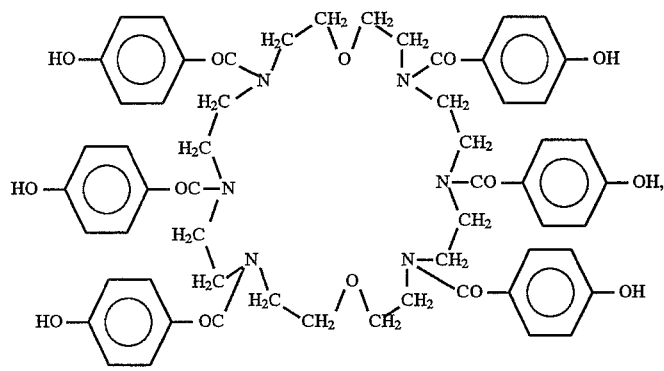
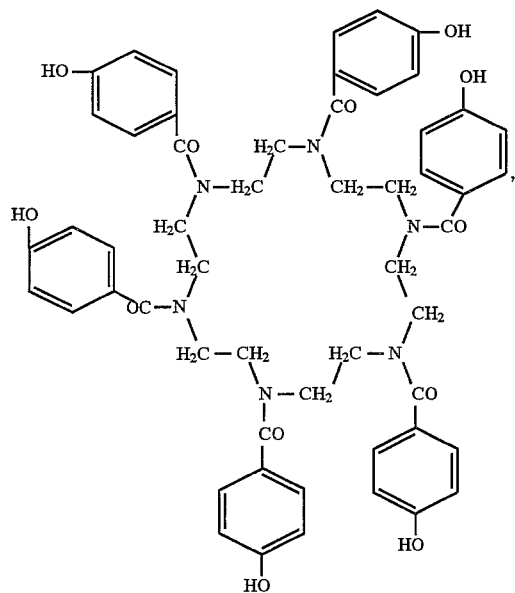

-continued
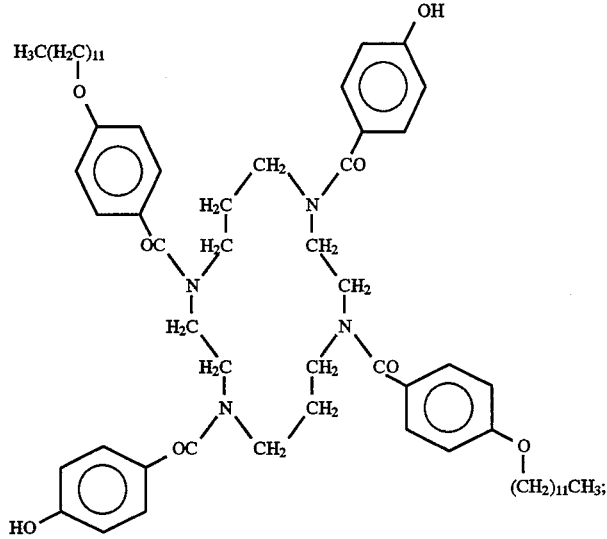
the cyclomultibenzylenes such as those represented by the formulas
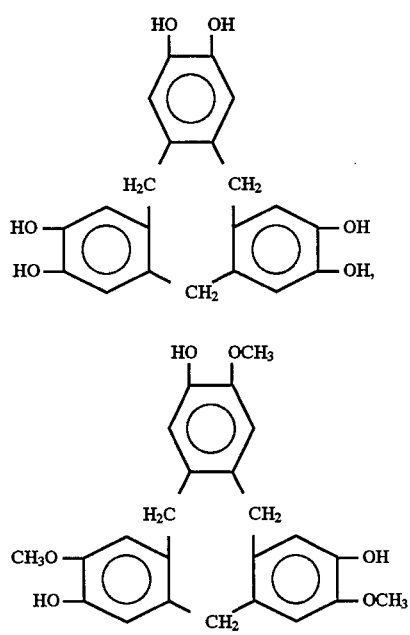
-continued
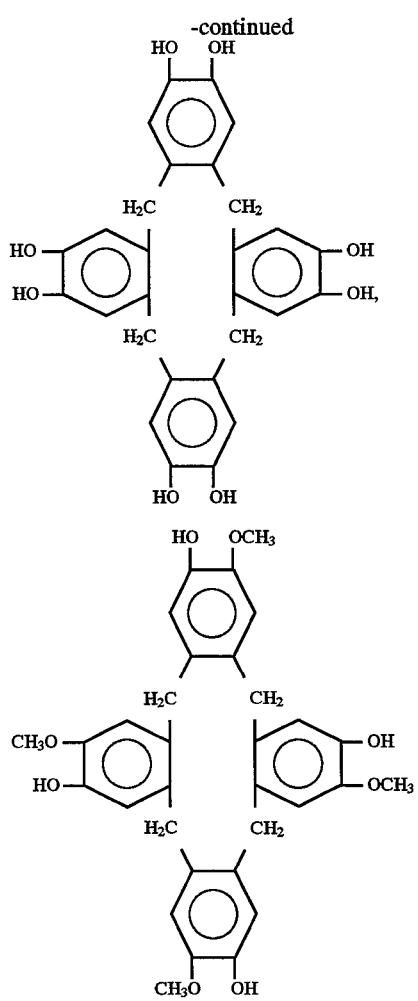

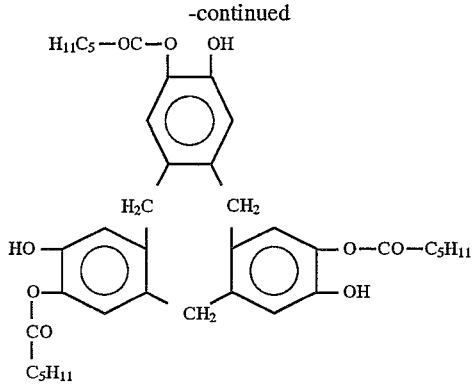
the metacyclophanes such as those represented by the formulas
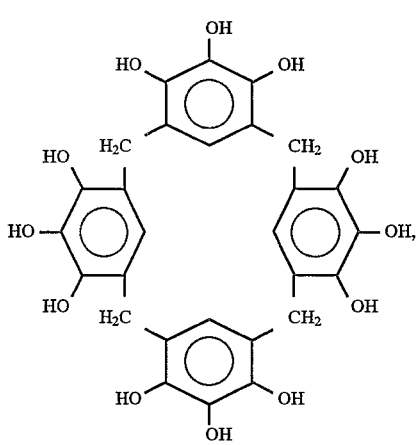
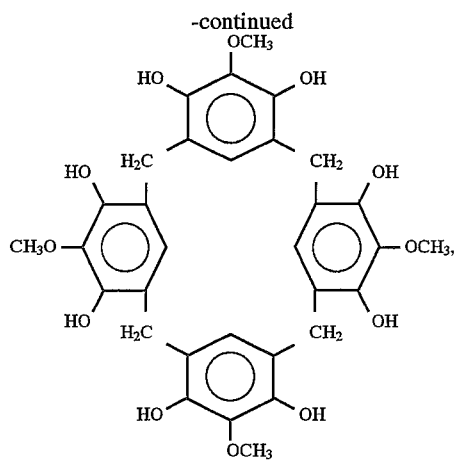
the anthraquinones such as those those represented by the formulas
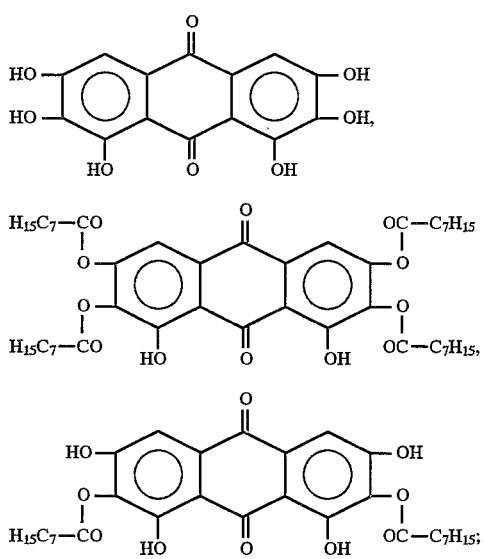
the tricycloquinazolines such as those represented by the formulas

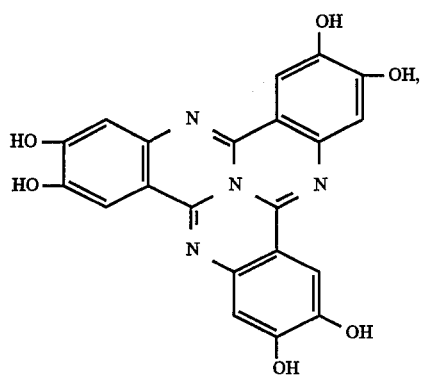
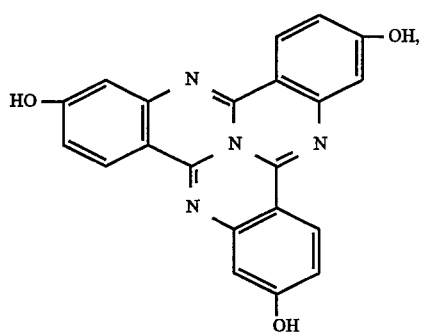
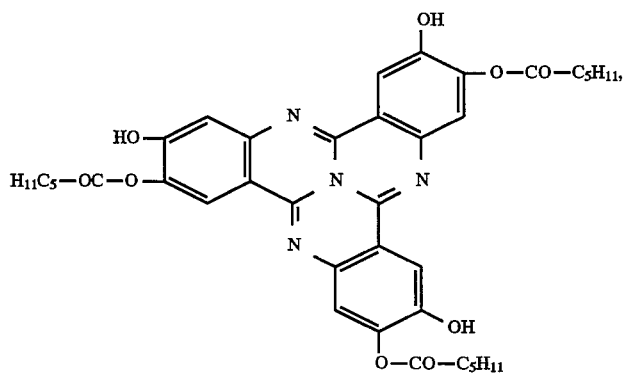
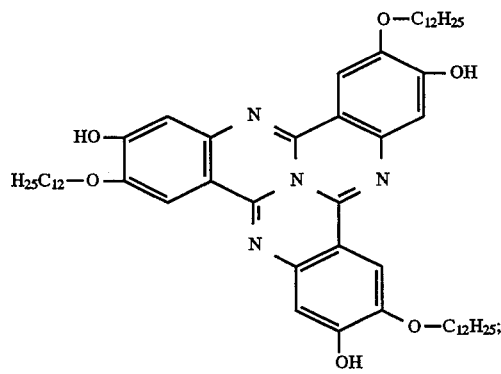
the bipyranylidenes such as those represented by the formulas

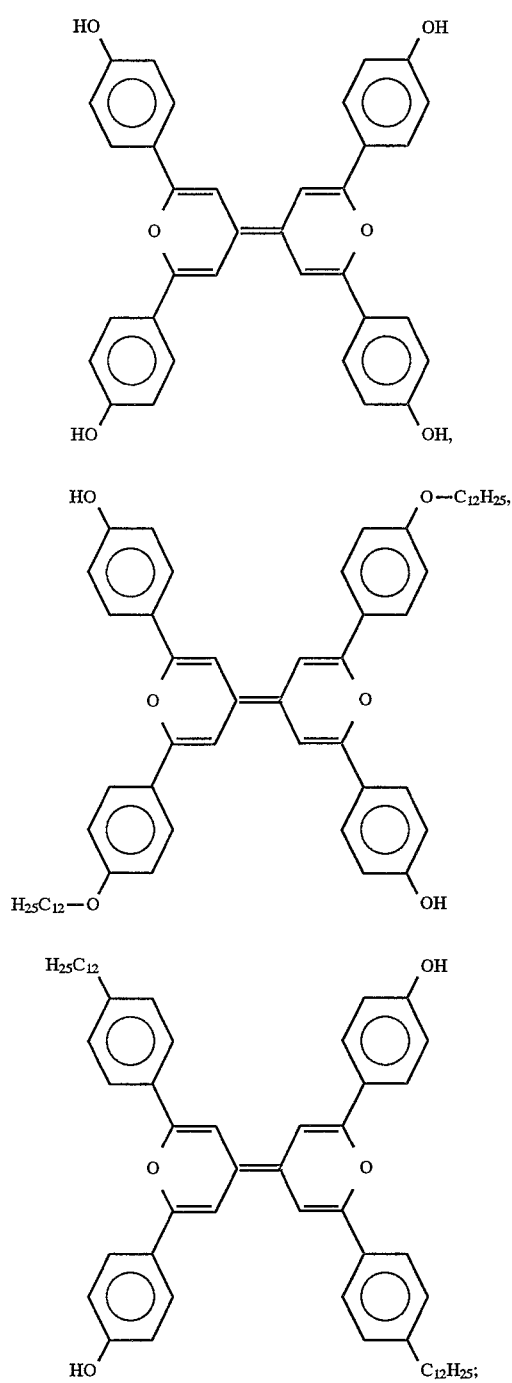
the bithiopyranylidenes such as those represented by the formulas
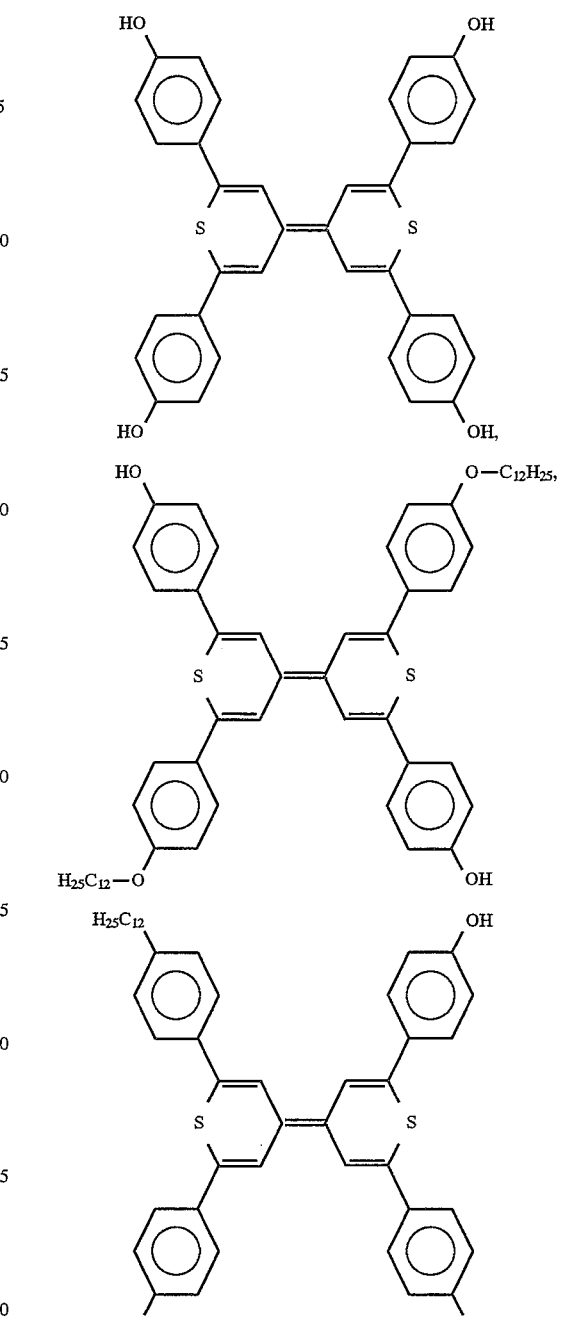
the triptycenes such as those represented by the formulas
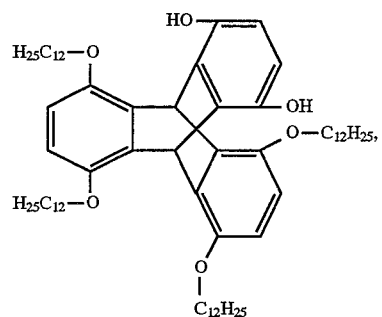

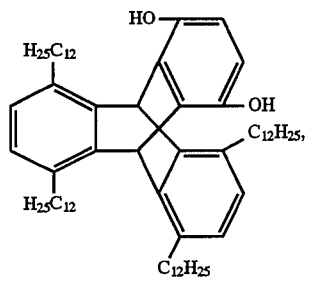
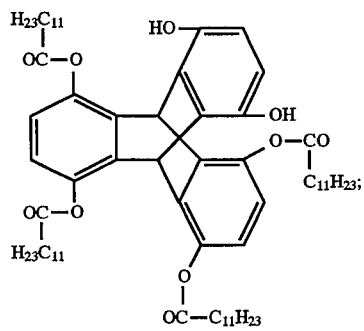
the bis[1,2-bis(phenyl)ethane-1,2-dithilato]metals such as those represented by the formulas
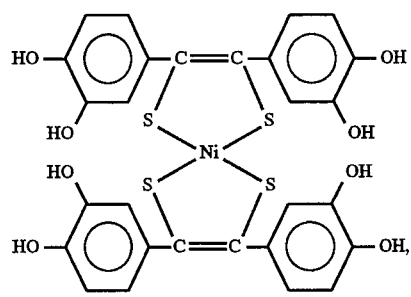
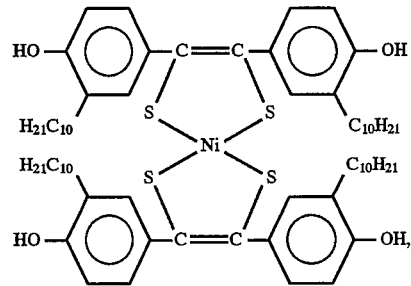
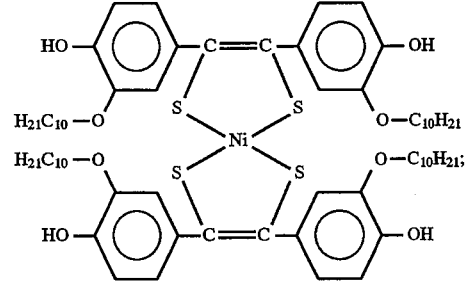
the bis($\beta$-diketonato)metal complexes those represented by the formulas
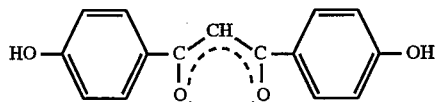
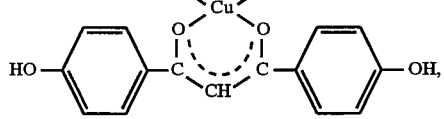
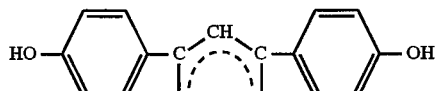
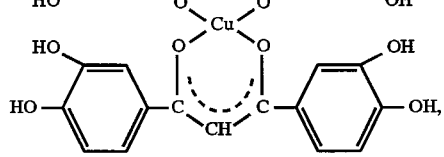
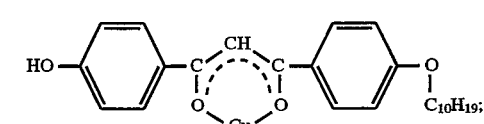
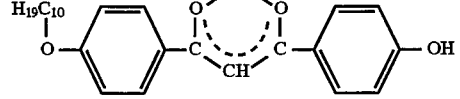
the (N-(4-hydroxy, alkoxy or alkyl substituted salicylidene) -4'-hydroxy, alkoxy or alkyl substituted aniline) copper (II) complexes such as those represented by the formulas
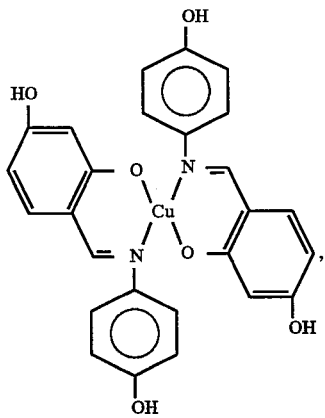

-continued
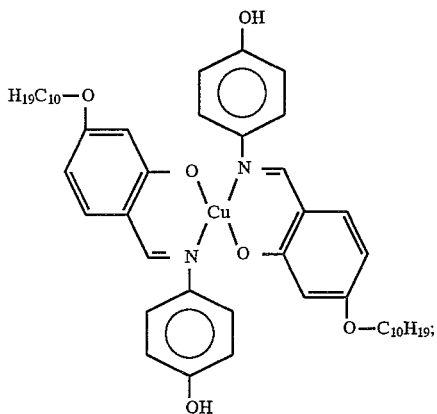
the triaryl pyrylium salts such as those represented by the formulas
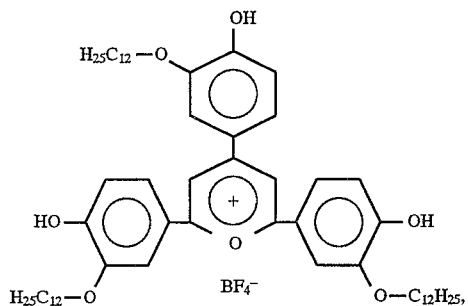
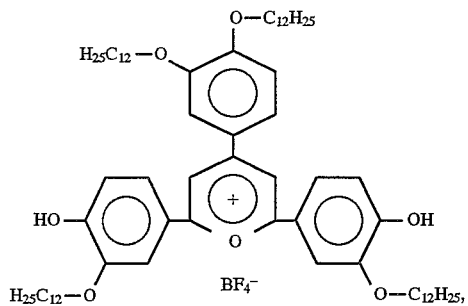
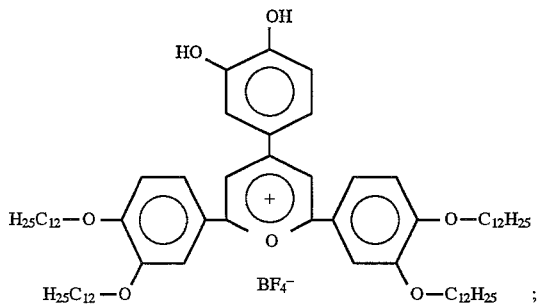
the decacyclenes such as those represented by the formulas
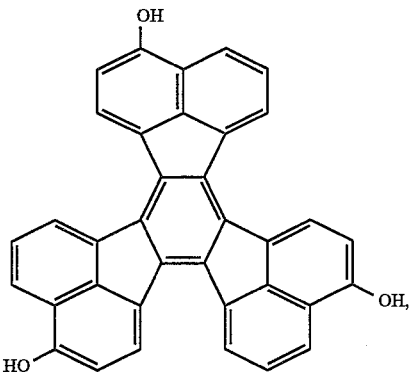
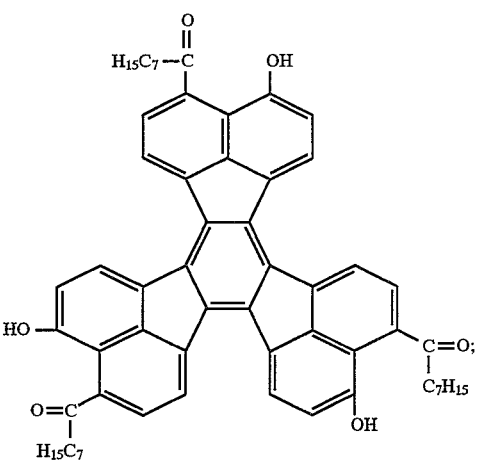
the dibenzopyrenes such as those represented by the formulas
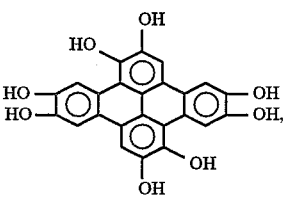
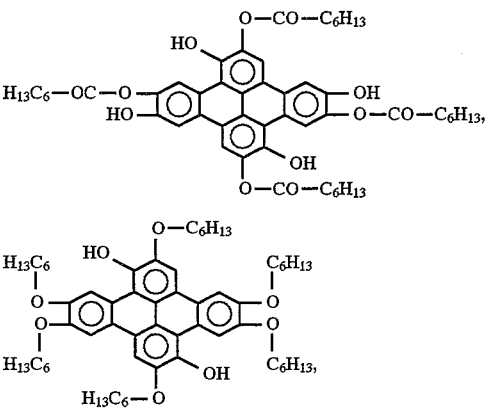

-continued

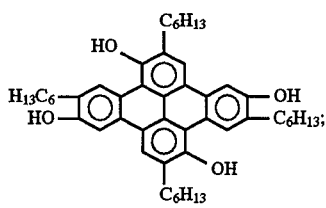

the tungsten-oxocalix[4]arenes such as those represented by the formulas

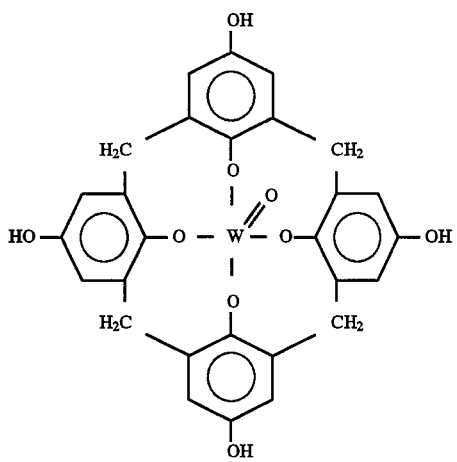

and the cis,cis-(3,5-dihydroxycyclohexyl)-3,4,5-tri(substituted)benzoates such as those represented by the formulas

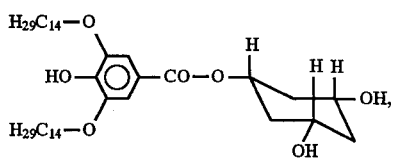

-continued

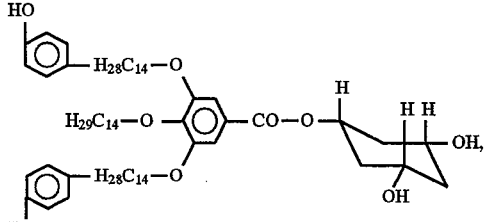

The hexa(4-substituted benzoates) of benzene, alkyl or substituted alkyl pentakis(phenylethynyl)phenyl ethers, hexakis((phenyl)alkynyl)benzenes, hexakis((phenyl) alkynyl)naphthylenes and hexakis(aryloxy)benzenes are generally prepared by aromatic nucleophilic substitution of halo groups on hexahalobenzenes, alkylation of hexa (haloalkyl)benzenes, etherification of pentabromophenol followed by palladium catalyzed carbon-carbon coupling with 4-substituted phenylacetylenes, bis (pentahaptocyclopentadienyl)cobalt catalyzed cyclotrimerization of a 1,4-di(4-substituted phenoxy)but-2-yne, $PdCl_2$ $(PhCN)_2$ catalyzed cyclotrimerization of a 1,2-di(4-substituted phenyl)acetylene, oxidation of hexamethylbenzene to the hexacarboxylic acid, reaction of hexa(hydroxy)benzene with 4-substituted benzoyl chlorides, reaction of hexafluorobenzene and the sodium salt of a phenol in 1,3-dimethyl-2-imidazolidinone solvent and palladium catalyzed alkynylation of hexabromobenzene or hexabromonaphthalene with an (alkynylphenyl)acetylene.

Methods for the synthesis of hexa(4-substituted benzoates) of benzene, alkyl or substituted alkyl pentakis (phenylethynyl)phenyl ethers, hexakis((phenyl)alkynyl) benzenes, hexakis((phenyl)alkynyl)naphthylenes and hexakis(aryloxy)benzenes are taught by C. Pugh and V. Percec, *J. Mater. Chem.*, volume 1, number 5, pages 765–773 (1991); F. C. Frank and S. Chandrasekhar, *J. Phys. (Paris)*, volume 41, number 11, pages 1285 –1288 (1980); M. Sorai, H. Yoshioka and H. Suga, *Mol. Cryst. Liq. Cryst.*, volume 84, numbers 1–4, pages 39–54 (1982); S. Takenata, K. Nishimura and S. Kysabayashi, *Mol. Cryst. Liq. Cryst.*, volume III, numbers 3–4, pages 227–236 (1984); D. M. Collard and C. P. Lillya, *J. Org. Chem.*, volume 56, pages 6064–6066 (1991); K. Praefeke, B. Kohne and D. Singer, *Angew. Chem. Int. Ed. Engl.*, volume 29, number 2, pages 177–179 (1990); B. Kohne and K. Praefcke, *Chimia*, volume 41, 196 (1987); and C. J. Gilmore, D. D. MacNicol, A. Murphy and M. S. Russell, *Tetrahedron Letters*, volume 24, number 31, pages 3269–3272 (1983); Chandrasekhar, S., Sadashiva, B. K. and Suresh, K. A., *Pramana*, volume 7, 471 (1977); Janietz, D., Praefike, K. and Singer, D., *Liq. Crystals*, volume 13, number 2, 247 (1993); all of which are incorporated herein by reference.

The triphenylenes, azatriphenylenes, hexa(4-substituted benzoates) of triphenylene and multi((phenyl)alkynyl) triphenylenes are generally prepared by reaction of veratrole, chloranil and 70% v/v aqueous sulfuric acid or by

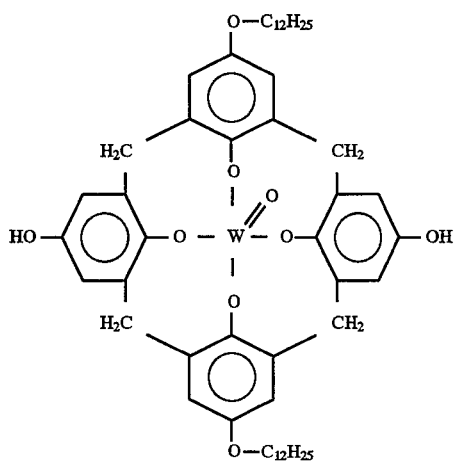

reaction of veratrole, ferric chloride and water to give 2,3,6,7,10,11,-hexamethoxytriphenylene (demethylation with hydrobromic acid and acetic acid or boron tribromide and benzene provides the corresponding hexaphenol). Reaction of the Grignard reagent from 4,4'-dimethyl-2-fluoro-2'-iodobiphenyl and magnesium using tetrahydrofuran solvent with o-fluorobromobenzene, 4-chloro-3-iodotoluene, 4-chloro-3-iodoanisole, 3-chloro-2-iodotoluene or 2-fluoro-3,5-dimethylbromobenzene gives 2,7-dimethyltriphenylene, 2,6,11-trimethyltriphenylene, 6,11-dimethyl-2-methoxytriphenylene, 1,6,11-trimethyltriphenylene or 1,3,6,11-tetramethyltriphenylene, respectively. Reaction of the organo lithium compound from 4,4'-dimethyl-2-fluoro-2'-iodobiphenyl and n-butyllithium using ether solvent with o-fluorobromobenzene, 4-chloro-3-iodotoluene or 2-fluoro-4,5-dimethylbromobenzene gives 2,7-dimethyltriphenylene, 2,6,11-trimethyltriphenylene and 2,3,6,11-tetramethyltriphenylene, respectively. Oxidation of the methyl group provides the carboxylic acid group while demethylation of the methoxy group provides the phenolic hydroxyl group. Reaction of 3,4,3',4'-tetrapentoxybenzil, potassium t-butoxide and acetone in ethanol solvent provides 3,4-bis(3,4-dipentoxyphenyl)-4-hydroxy-2-cyclopenten-1-one. Elimination of water produces the corresponding cyclopentadienone which then is reacted with dimethyl acetylenedicarboxylate in chlorobenzene solvent to provide the Dieis-Alder adduct, dimethyl-3,4,3",4"-tetrapentoxy-o-terephenyl-4',5'-dicarboxylate. Photolysis with iodine in benzene solvent provides 6,7,10,11-tetrapentoxytriphenylene-2,3-dicarboxylate. Demethylation of the methoxy group provides the phenolic hydroxyl group while hydrolysis of the carboxylic acid ester group provides the carboxylic acid group. Reaction of triphenylene with excess bromine using iron powder as catalyst and nitrobenzene solvent provides 2,3,6,7,10,11-hexabromotriphenylene. Nucleophilic aromatic substitution of the hexabromotriphenylene provides access to numerous substituted triphenylenes. Thus, reaction of a sodium alkyl thiolate in dimethylethylideneurea solvent with 2,3,6,7,10,11-hexabromotriphenylene provides a 2,3,6,7,10,11-hexa(alkylthio)triphenylene. Reaction of sodium hydrosulfide with 2,3,6,7,10,11-hexabromotriphenylene provides a 2,3,6,7,10,11-hexamercaptotriphenylene. Reaction of $Cu_2Br_2$, Cu powder, ethylenediamine (excess serves as solvent) with 2,3,6,7,10,11-hexabromotriphenylene provides 2,3,6,7,10,11-tris(N,N'-ethylenediamino)triphenylene. Reaction of hexaketocyclohexane octahydrate and diaminomaleonitrile in acetic acid provides hexaazatriphenylenecarbonitrile which is then hydrolyzed to hexaazatriphenylenehexacarboxamide in concentrated sulfuric acid. The hexaazacarboxamide is then in turn subjected to diazotizing conditions by treatment of a solution in trifluoroacetic acid with sodium nitrite, the precipitation of the sodium salt followed by acidification with HCl to provide hexaazatriphenylenehexacarboxylic acid. Hexaazatriphenylenehexacarboxylic acid trianhydride is prepared by treatment of the hexaazacarboxylic acid with acetic anhydride at 115°±2° C. for 10 minutes. Multi((phenyl)alkynyl)triphenylenes are prepared by palladium catalyzed alkynylation of a hexahalotriphenylene, such as 2,3,6,7,10,11-hexabromotriphenylene with an (alkynylphenyl)acetylene. Reaction of hexa(hydroxy)triphenylene with 4-substituted benzoyl chlorides provides hexa(4-substituted benzoates) of triphenylene.

Methods for the synthesis of triphenylenes, azatriphenylenes, and multi((phenyl)alkynyl)triphenylenes are taught by the aforementioned Collard and Lillya reference; the aforementioned Praefcke, Kohne and Singer reference; H. Ringsdorf, R. Wustefeld, E. Zerta, M. Ebert and J. H. Wendorff, Angew. Chem. Int. Ed. Engl., volume 28, number 7, pages 914–918 (1989); R. Breslow, B. Jaun, R. Q. Kluttz and C-Z. Xia, Tetrahedron, volume 38, number 6, pages 863–867 (1982); H. Heaney and P. Lees, Tetrahedron Letters, number 41, pages 3049–3052 (1964); K. D. Bartle, H. Heaney, D. W. Jones and P. Lees, Tetrahedron, volume 21, pages 3289–3296 (1965); G. Wenz, Makromol. Chem., Rapid Commun., volume 6, pages 577–584 (1985); Chemical Abstracts 114:165140; M. Sorai, S. Asahina, C. Destrade and N. H. Tinh, Liquid Crystals, volume 7, number 2, pages 163–180 (1990); K. Kanakarajan and A. W. Czarnik, American Chemical Society, Polymer Preprints, volume 29, pages 246–247 (1988); K. Kanakarajan and A. W. Czarnik, J. Org. Chem., volume 51, pages 5241–5243 (1986); W. K. Lee, P. A. Heiney, J. P. McCauley, Jr. and A. B. Smith III, Mol. Cryst. Liq. Cryst., volume 198, page 273–284 (1991); M. Piattelli, E. Fattorusso, R. A. Nicolaus and S. Magno, Tetrahedron, volume 21, pages 3229–3236 (1965); W. Kreuder, H. Ringsdorf and P. Tschirner, Makromol. Chem., Rapid Commun., volume 6, pages 367–373 (1985); M. Werth, S. U. Vallerien and H. W. Spiess, Liquid Crystals, volume 10, number 6, pages 759–770 (1991); H. Bengs, O. Karthaus, H. Ringsdorf, C. Baehr, M. Ebert and J. H. Wendorff, Liquid Crystals, volume 10, number 2, pages 161–168 (1991); O. Karthaus, H. Ringsdorf, M. Ebert and J. H. Wendorff, Makromol. Chem., 193, pages 507–513 (1992); W. Kranig, C. Boeffel, H. W. Spiess, Macromolecules, volume 23, pages 4061–4067 (1990); B. Huser and H. W. Spiess, Makromol. Chem., Rapid Commun., volume 9, pages 337–343 (1988); T-C. Hsu, B. Huser, T. Pakula, H. W. Spiess and M. Stamm, Makromol. Chem., volume 191, pages 1597–1609 (1990) and W. Kreuder and H. Ringsdorf, Makromol. Chem., Rapid Commun., volume 4, pages 807–815 (1983); Tinh, N. H., Destrade, C. and Gasparoux, H., Physics Lett. A, 72, 251 (1979); Destrade, C., Bernaud, M. C., Gasparoux, H., Levelut, A. M. and Tinh, N. H., (S. Chandrasekhar, ed.), Proceedings International Conference Liquid Crystals, Bangalore (Heyden), 29 (1980); all of which are incorporated herein by reference.

The truxenes, trithiatriuxenes, trioxatruxenes, triazatruxenes and triketotruxenes are generally prepared by trimerization reaction of 5-monosubstituted-, 6-monosubstituted-, or 5,6-disubstituted-2H-benzothiophene-3-ones; 5-monosubstituted-, 6-monosustituted- or 5,6-disubstituted-2H-benzofuran-3-ones; or 5-monosubstituted-, 6-monosubstituted-, or 5,6-disubstituted-1-indanones in thylpolyphosphate. Oxidation of 5- and/or 6-methyl groups provides the carboxylic acid group(s) while demethylation of 5 and/or 6-methoxy groups (in pyridine hydrochloride at 240° C. for 30 minutes under nitrogen) provides the phenolic hydroxyl group(s). Trimerization reaction of 5-monosubstituted-, 6-monosubstituted- or 5,6-disubstituted-1-methoxyindan-3-ones in ethyl polyphosphate followed by demethylation of the 1-methoxy group, then oxidation of the resultant secondary alcohol group (using $CrO_3$ in acetic acid, or $CrO_3$ in pyridine, $KMnO_4$ or $K_2Cr_2O_7$) to the keto group provides triketotruxenes.

Methods for the synthesis of the truxenes, trithiatriuxenes, trioxatruxenes, triazatruxenes and triketotruxenes are taught by W. K. Lee and P. A. Heiney, Liquid Crystals, volume 8, number 6, 839–850 (1990); N. H. Tinh, R. Cayuela and C. Destrade, Mol. Cryst. Liq. Cryst., volume 122, pages 141–149 (1985); R. Cayuela, H. T. Nguyen, C. Destrade and A. M. Levelut, Mol. Cryst. Liq. Cryst., volume 177, page 81–91 (1989); C. Destrade, J. Malthete, N. H. Tinh and H. Gasparoux, *Phys. Lett. A*78, number 1, pages 82–84 (1980); C. Destrade, H. Gasparoux, A. Babeau, N. H. Tinh and J. Malthete, *Mol. Cryst. Liq. Cryst.*, volume 67, numbers 1–2, pages 37–48 (1981); P. Foucher, C. Destrade, N. H. Tinh, J. Malthete and A. M. Levelut, *Mol. Cryst. Liq. Cryst.*, volume 108, numbers 3–4, pages 219–230 (1984) ; N. H. Tinh, J. Malthete and C. Destrade, *Mol. Cryst. Liq. Cryst. Lett.*, volume 64, pages 291–298 (1981); L. Mamlok, J. Malthete, N. H. Tinh, C. Destrade and A. M. Levelut, *J. Phys. (Paris) Lett.*, volume 43, pages L-641–L-647 (September 1, 1982); A. M. Levelut, *J. Chim. Phys.*, volume 80, pages 149–161 (1983); H. T. Nguyen, L. Mamlok and J. Malthete, *Mol. Cryst. Liq. Cryst.*, volume 114, page 39 (1984); and J. Le Jay and M. Pesquer, *Mol. Cryst. Liq. Cryst.*, volume 95, numbers 1–2, (1983); all of which are incorporated herein by reference.

The phthalocyanines, metallophthalocyanines, porphyrins and metalloporphyrins are generally prepared by refluxing 1,3-diimino-5,6-substituted-1,3-dihydroisoindoles in dimethylaminoethanol (the copper containing phthalocyanine is obtained by refluxing the free phthalocyanine and copper (I) cyanide in dimethylformamide); refluxing 1,2-dicyano-4,5-substituted benzenes in 1-(dimethylamino)-2-propanol, treating the free phthalocyanine with the lithium salt of 1-pentanol to give the dilithium derivative followed by reaction with this anhydrous salt to give the corresponding divalent metallic complex; or reaction of pyrrole and a benzaldehyde (Rothemund reaction) in pyridine, for example pyrrole with p-methoxybenzaldehyde, to give the subsitiuted tetraphenylporphine (demethylation with hydrobromic acid provides the a, b, g, d-tetra-p-hydroxyphenylporphine). N-methylation is accomplished via treatment of solutions (usually in chloroform) with methyl fluorosulphate or methyl iodide. Metalation reaction of porphyrins to give metalloporphyrins generally involves reaction of the free porphyrin with a metal salt ($MX_2$) in a solvent (such as acetic acid, pyridine, phenol, benzonitrile, dimethyformamide, decalin, diethylether, ethanol and combinations thereof). An additional specific preparation of octa(4-substituted phenyl)phthalocyanines and metallophthalocyanines involves (A) reaction of a 4,4'-disubstituted benzil, acetone and potassium t-butoxide in ethanol and tetrahydrofuran solvents, (B) reaction of the 3,4-bis(4-substituted phenyl)-4-hydroxy-2-cyclopenten-1-one product thus obtained with dicyanoacetylene in chlorobenzene solvent and, (C) reaction of the 4,4'-disubstituted-o-terephenyl-4',5'-dicarbonitrile and 1,8-diazabicyclo[5.4.0]undec-7-ene to provide 2,3,9,10,16,17,23,24-octakis(4-substituted phenyl)-29H,31H-phthalocyanine. To obtain the copper phthalocyanine, copper (II) chloride in n-pentanol is added to the aforementioned reaction step (C).

Methods for the synthesis of the phthalocyanines, metallophthalocyanines, porphyrins and metalloporphyrins are taught by J. P. Collman, M. B. Zisk and W. A. Little, *Org. Supercond., (Proc. Int. Conf.)*, pages 317–324 (1990) edited by V. Z. Kresin and W. A. Little, Plenum, N.Y., N.Y.; G. Pawlowski and M. Hanack, *Synthesis*, pages 287–289 (April, 1980); C. Piechocki, J. Simon, A. Skoulios, D. Guillon and P. Weber, *J. Am. Chem. Soc.*, volume 104, number 19, pages 5245–5247 (1982); K. Ohta, T. Watanabe, H. Hasebe, Y. Morizumi, T. Fujimoto, I. Yamamoto, D. Lelievre and J. Simon, *Mol. Cryst. Liq. Cryst.*, volume 196, pages 13–26 (1991); J. W. Goodby, P. S. Robinson, B. K. Teo and P. E. Cladis, *Mol. Cryst. Liq. Cryst. Lett.*, volume 56, number 10, pages 303–309 (1980); D. Guillon, A. Skoulios, C. Piechocki, J. Simon and P. Weber, *Mol. Cryst. Liq. Cryst.*, volume 100, numbers 3–4, pages 275–284 (1983); D. Dolphin (ed.), *The Porphyrins, Volume I, Structure and Synthesis, Part A* published by Academic Press, N.Y., N.Y. (1978); D. Dolphin (ed.), *The Porphyrins, Volume II, Structure and Synthesis, Part B*, published by Academic Press, N.Y., N.Y. (1978); A. Triebs and N. Haberle, *J. Liebigs Ann. Chem.*, volume 718, pages 183–207 (1968); J. P. Collman, R. R. Gagne, C. A. Reed, T. R. Halbert, G. Lang and W. T. Robinson, *J. Am. Chem. Soc.*, 97:6, 1427–1439 (3-19-1975); D. K. Lavallee and A. E. Gebala, *Inorg. Chem.*, 13, 8, 2004–2008 (1974); R. Grigg, A. Sweeney, G. R. Dearden, A. H. Jackson and A. W. Johnson, *J. Chem. Soc., Chem. Commun.*, 20, 1273–1274 (10-21-1970); H. M. G. Al-Hazimi, A. H. Jackson, A. W. Johnson and M. Winter, *J. Chem. Soc., Perkin Trans. I*, 98–103 (1977); P. Rothemund, *J. Am Chem. Soc.*, 58, 625–627 (1936); J. B. Kim, J. J. Leonard and F. R. Lange, *J. Am. Chem Soc.*, 94:11, 3986–3993 (5-31-1972); D. W. Thomas and A. E. Martell, *J. Am. Chem. Soc.*, 78, 1335–1338 (4-5-1956); L. K. Gottwald and E. F. Ullman, *Tet. Lett.*, 36, 3071–3074 (1969); K. Ohta, T. Watanabe, S. Tamaka, T. Fujimoto, I. Yamamoto, P. Bassoul, N. Kucharczyk and J. Simon, *Liquid Crystals*, 10, 3 357–368 (1991) and W. T. Ford, *Polymer Liquid Crystals with Side Chain Discogens*, Office of Naval Research Report No. 90 02 12067 (2-5-90); all of which are incorporated herein by reference.

The macrocyclic polyamines are generally prepared by the following sequential reactions: (A) a polyalkylenepolyamine, such as diethylenetriamine, is reacted with p-toluenesulfonyl chloride in pyridine to provide the poly(N-tolylsulfonyl) analog, such as N,N',N"-tris(p-tolylsulfonyl)diethylenetriamine, (B) the poly(N-tolylsulfonyl)triamine in ethanol is reacted with sodium ethoxide dissolved in ethanol to provide the disodium salt of the poly(N-tolylsulfonyl)triamine, such as N,N',N"-tris(p-tolylsulfonyl)diethylene-N,N"-disodium salt, (C) the disodium salt, ethylene carbonate and catalytic potassium hydroxide are reacted to provide the diol of the poly(N-tolysulfonyl)triamine, such as 3,6,9-tris(p-tolylsulfonyl)-3,6,9-triazaundecane-1,11-diol, (D) the diol of the poly(N-tolylsulfonyl)triamine in triethylamine and methylene chloride is reacted with methanesulfonyl chloride to provide the dimethanesulfonate of the diol of the poly(N-tolylsulfonyl)triamine, such as 3,6,9-tris(p-tolylsulfonyl)-3,6,9-triazaundecane-1,11-dimethanesulfonate, (E) the disodium salt of the poly(N-tolylsulfonyltriamine in dimethylformamide and the dimethanesulfonate of the diol of the poly(N-tolylsulfonyl)triamine are reacted to provide the cyclic polyamine with N-tolylsulfonyl groups, such as 1,4,7,10,13,16-hexakis(p-tolylsulfonyl)-1,4,7,10,13,16-hexaazacyclooctadecane, (F) the cyclic polyamine with N-tolylsulfonyl groups is reacted with concentrated sulfuric acid to provide the polyhydrosulfate salt which is added to water then neutralized with aqueous sodium hydroxide to provide the cyclic polyamine, such as 1,4,7,10,13,16-hexaazacyclooctadecane. The N-tolylsulfonyl groups may also be removed via reaction with 30% HBr in acetic acid in the presence of a large excess of phenol to provide the poly(hydrogen bromide) salt. The free cyclic polyamine may also be obtained from the poly(acid) salt via neutralization over a basic ion exchange resin. Macrocyclic amine ethers are prepared via the aforementioned reaction, for example, via substitution of an ether containing alkylene amine compound, such as bis(aminoethyl)ether, for the polyalkylenepolyamine.

Methods for the synthesis of the macrocyclic polyamines are taught by the aforementioned Ford reference, J-M. Lehn, S. H. Pine, E. Watanabe and A. K. Willard, *J. Am. Chem. Soc.*, volume 99 pages 6766–6768 (1977); J. Comarmond, P. Plumere, J-M. Lehn, Y. Agnus, R. Louis, R. Weiss, O. Kahn and I. Morgenstern-Badarau, *J. Am. Chem. Soc.*, volume 104, pages 6330–6340 (1982), C. Mertesdorf and H. Ringsdorf, *Liquid Crystals*, volume 5, number 6, pages 1757–1772 (1989); C. Mertesdorf, H. Ringsdorf and J. Stumpe, *Liquid Crystals*, volume 9, number 3, pages 337–357 (1991); G. W. Gokel and S. H. Korzeniowski, *Macrocyclic Polyether Synthesis* published by Springer-Verlag, Berlin, Germany (1982); B. Dietrich, M. W. Hosseini, J-M. Lehn and R. B. Sessions, *Helvetica Chimica Acta*, volume 66, pages 1262–1278 (1983); T. J. Atkins, J. E. Richman and W. F. Oettle in *Organic Synthesis*, W. A. Sheppard (ed.), published by John Wiley and Sons, N.Y., N.Y., volume 78, pages 86–98 (1978); J. E. Richman and T. J. Atkins, *J. Am. Chem Soc.*, volume 97, pages 2268–2270 (1974) and J-M. Lehn, J. Malthete and A-M. Levelut, *J. Chem. Soc., Chem. Commun.*, pages 1794–1796 (1985); all of which are incorporated herein by reference.

The cyclomultibenzylenes are generally prepared by trifluoroacetic acid catalyzed electrophilic cyclotetramerization of 3,4-bis(substituted)benzyl alcohols or perchloric acid catalyzed cyclotrimerization of the phenolic allyl ether of vanillyl alcohol followed by allyl ether cleavage to the phenol.

Methods for the synthesis of the cyclomultibenzylenes are taught by V. Percec, C. G. Cho, C. Pugh and D. Tomazos, *Macromolecules*, volume 25, pages 1164–1176 (1992); W. Kranig, H. W. Spiess and H. Zimmermann, *Liquid Crystals*, volume 7, number 1, pages 123–129 (1990); J. Malthete and A. Collet, *J. Am. Chem. Soc.*, volume 109, pages 7544–7545 (1987); A. Collet and G. Gottarelli, *J. Am. Chem. Soc.*, volume 103, pages 5912–5913(1981); J. Canceill, A. Collet and G. Gottarelli, *J. Am. Chem. Soc.*, volume 106, pages 5997–6003 (1984); J. Canceill, J. Gabard and A. Collet, *J. Chem. Soc., Chem. Commun.*, 122–123 (1983) and R. Boss and R. Scheffold, *Angew. Chem., Int. Ed. Engl.*, 15, 558–559 (1976); all of which are incorporated herein by reference.

The metacyclophanes are generally prepared by acid catalyzed condensation of pyrogallol with 1,1-diethoxyethane, acid catalyzed condensation of pyrogallol with propionaldehyde, acid catalyzed condensation of resorcinol with acetaldehydes or acid catalyzed condensation of pyrogallol with paraformaldehyde followed by treatment with butyrylchloride then hydrolysis to the phenol.

Methods for the synthesis of the metacyclophanes are taught by L. M. Tunstad, J. A. Tucker, E. Dalcanale, J. Weiser, J. A. Bryant, J. C. Sherman, R. C. Hegelson, C. B. Knoblet and O. J. Cram, *J. Org. Chem.*, 54,1305 (1989); G. Cometti, E. Dalcanale, A. Du Vosel and A-M. Levelut, *J. Chem. Soc., Chem. Commun.*, pages 163–165 (1990); S. Bonsignore, G. Cometti, E. Dalcanale and A. DuVosel, *Liquid Crystals*, volume 8, number 5, pages 639–649 (1990) and G. Cometti, E. Dalcanale, A. Du Vosel and A-M. Levelut, *Liquid Crystals*, volume 11, number 1, pages 93–100 (1992); all of which are incorporated herein by reference.

The anthraquinones are generally prepared by oxidation of anthracenes, for example, using $CrO_3$ or ceric ammonium sulfate; cyclization of o-aroylbenzoic acids; treatment of $H_2SO_4$ solutions of benzanthraquinones diluted into water with $KMnO_4$ to give anthraquinone polycarboxylic acids as the oxidation products; intramolecular Friedel-Crafts acylation of diphenylmethane o-monocarboxylic acid compounds followed by oxidation of the anthrone thus formed and reaction of phthalides and arynes to give 10-hydroxyanthones which are then oxidized.

Methods for the synthesis of the anthraquinones are taught by J. Billard, J. C. Dubois, C. Vauchier and A-M. Levelut, *Mol. Cryst. Liq. Cryst.*, volume 66, numbers 1–2, -pages 115–122 (1981); B. S. Furniss, A. J. Hannaford, V. Rogers, P. W. G. Smith and A. R. Tatchell, *Vogel's Textbook of Practical Organic Chemistry* published by Longman Group Limited, Essex, England, pages 778–781 (1978); J. March, *Advanced Organic Chemistry* published by John Wiley and Sons, N.Y., N.Y., page 1081 (1985); E. Muller and Otto Bayer, *Methoden Der Organischem Chemie (Houben-Weyl)* published by Georg Thieme, Stuttgart, Germany, Band VII/3c (1979); J W. Cook, *J. Chem. Soc,*, 2529–2532 (1931); J. W. Cook, *J. Chem. Soc.*, 1592–1597 (1933); A. S. Kende and G. P. Rizzi, *J. Am. Chem. Soc.*, 103, 4247 (1981); G. H. Posner, M. J. Chapdelaine and C. M. Lentz, *J. Org. Chem.*, 44, 3661 (1979); P. G. Sammes and T. W. Wallace, *J. Chem. Soc.*, Perkin Trans. 1, 1377 (1975) and C. A. Townsend, P. R. O. Whittamore and S. W. Brobst, *J. Chem. Soc.*, Chem. Commun., 726 (1988); all of which are incorporated herein by reference.

The tricycloquinazolines are generally prepared by via trimerization of a halo or polyhaloanthranil using ammonium acetate, acetic acid and sulpholane, followed by aromatic nucleophilic substitution of halo groups. Direct nitration of tricycloquinazoline using fuming nitric acid in sulfuric acid provides 1,3,6,8,11,13-hexanitrotricycloquinazoline which may then be reduced to the hexaamine.

Methods for the synthesis of the tricycloquinazolines are taught by E. Keinan, S. Kumar, S. P. Singh, R, Ghirlando and E. J. Wachtel, *Liquid Crystals*, volume 11, number 2, pages 157–173 (1992) and F. Yoneda and K. Mera, *Chem. Pharm. Bull.*, volume 21, number 7, pages 1610–1611 (1973); all of which are incorporated herein by reference.

The bipyranylidenes are generally prepared by reaction of a pyrylium salt and tributylphoshine or by reaction of a pyrylium salt and zinc in acetonitrile.

Methods for the synthesis of the bipyranylidenes are taught by F. D. Saeva, G. A. Reynolds and L. Kaszczuk, *J. Am. Chem. Soc.*, 104, 3524–3525 (1982); C. Fabre, R. Fugnitto and H. Strzelecka. *Compt. rend.*, 282C, 175 (1976); G. A. Reynolds and C. H. Chen, *J. Heterocycl. Chem,,* 18, 1235 (1981) and R. Fugnitto, H. Strzelecka, A. Zann, J. C. Dubois and J. Billard, *J. C. S. Chem. Comm.*, 271–272 (1980); all of which are incorporated herein by reference.

The bithiopyranylidenes are generally prepared by reaction of a thiopyrylium salt and zinc in acetonitrile.

Methods for the synthesis of the bithiopyranylidenes are taught by R. Fugnitto, H. Strzelecka, A. Zann, J. C. Dubois and J. Billard, *J. C. S, Chem. Comm.*, 271–272 (1980); V. Gionis, R. Fugnitto, G. Meyer, H. Strzelecka and J. C. Dubois, *Mol. Cryst. Liq. Cryst.*, 90, 153 (1982) and H. Strzelecka, V. Gionis, J. Rivory and S. Flandrois, *J. Phys., Colloq., (C3*, Colloq. Int. CNRS Phys. Chim. Met. Synth. Org.) 1201–1206 (1982); all of which are incorporated herein by reference.

The triptycenes are generally prepared by Dieis-Alder reaction between benzoquinone and an anthracene or a benzyne and an anthracene. Treatment of the Dieis-Alder adduct of p-benzoquinone and anthracene with HBr provides the diphenol, triptycenequinol. Electrophilic substitution on the aromatic rings of triptycene may be performed. Heating of triptycene with fuming nitric acid provides a mixtiure of 2,6,12- and 2,7,13-trinitrotriptycenes which may be reduced to the corresponding triamines.

Methods for the synthesis of the triptycenes are taught by S. Norvez and J. Simon, *J. Chem. Soc., Chem. Commun.*, 1398–1399 (1990); S. Norvez, *J. Org. Chem.*, 58, 2414–2418 (1993); and V. R. Skvarchenko, V. K. Shalaev and E. I. Klabunovskii, *Russian Chemical Reviews*, 43 (11), 951–966 (1974); all of which are incorporated herein by reference.

The bis[1,2-bis(phenyl)ethane-1,2-dithiolato metals are generally prepared by reacting a substituted benzil with phosphorus pentasulfide then a transition metal salt.

Methods for the synthesis of the bis[1,2-bis(phenyl)ethane-1,2-dithiolato metals are taught by I. Yamamoto, K. Ota and H. Takatsu, Jpn. Kokai, Tokkyo Koho JP 02,218,662 (8-31-90); which is incorporated herein by reference.

The bis($\beta$-diketonato)metal complexes are generally prepared by reaction of a 1,3-di(4-substituted phenyl)propane-1,3-dione and a salt of a metal halide, such as $CuCl_2 \cdot 2H_2O$, potassium hydroxide in ethanol to provide the bis[1,3-di(4-substituted phenyl)propane-1,3-dionato]metal(II).

Methods for the synthesis of the bis(b-diketonato)metal complexes are taught by A. M. Giroud-Godquin and J. Billard, *Mol. Cryst. Liq. Cryst.*, 66, 147 (1981); K. Ohta, A. Ishii, I. Yamamoto and K. Matsuzaki, *J. Chem. Soc., Chem. Commun.*, 1099–1101 (1984); B. K. Sadashiva and S. Ramesha, *Mol. Cryst. Liq. Cryst. Bulletin*, 1, 219 (1986) and K. Ohta, H. Muroki, A. Takagi, K. Hatada, H. Ema, I. Yamamoto and K. Matsuzak, *Mol. Cryst. Liq. Cryst. Bulletin*, 1, 198–199 (1986); all of which are incorporated herein by reference.

The (N-(4-hydroxy, alkoxy or alkyl substituted salicylidene)-4'-hydroxy, alkoxy or alkyl substituted aniline) copper (II) complexes are generally prepared by reacting a 4-substituted-2-hydroxybenzaldehyde with Cu(OAc)$_4 \cdot 2H_2O$ in ethanol as a boiling solution for 2.5–3 hours; followed by reaction of the resultant bis(carbonyl)copper (II) complex with a 4-substituted aniline in refluxing ethanol for 30 hours.

Methods for the synthesis of the (N-(4-hydroxy, alkoxy or alkyl substituted salicylidene)-4'-hydroxy, alkoxy or alkyl substituted aniline) copper (II) complexes are taught by M. Marcos, P. Romero and J. L. Serrano, *Mol. Cryst. Liq. Cryst.*, 167, 123–134 (1989).

The triaryl pyrylium salts are generally prepared by acidic condensation ($HClO_4$, $HBF_4$) of an acetophenone with a chalcone in acetic anhydride solvent.

Methods for the synthesis of the triaryl pyrylium salts are taught by A. R. Katritzky, O. A. Schwarz, A. E. A. Rahman, D. E. Leahy, *J. Heterocycl. Chem.*, 21,1673–1677 (Nov.-Dec., 1984); D. Markovitsi, I. Lecuyer, B. Clergeot, C. Jallabert, H. Strzelecka and M. Veber, *Liquid Crystals*, 6, 1, 83–92 (1989) and P. Davidson, C. Jallabert, A. M. Levelut, H. Strzelecka and M. Veber, *Liquid Crystals*, 3, 1, 133–137 (1988); all of which are incorporated herein by reference.

The decacyclenes are generally prepared using commercially available decacyclene. Thus, nitration followed by reduction provides the arylamine group. Diazotization of the aryl amine group followed by hydrolysis of the diazonium salt provides the phenolic hydroxyl group. Sulfonation followed by alkali fusion of the sulfonate provides the phenolic hydroxyl group. Reation of the neutral diazonium salt solution with cuprous cyanide followed by hydrolysis of the nitrile provides the carboxylic acid group. Friedel-Crafts alkylation provides the alkyl group. Oxidation, for example of the methyl alkyl group, provides the carboxylic acid group. Friedel-Crafts acylation provides the ketone group.

Methods for the synthesis of the decacyclenes are taught by E. Keinan, S. Kumar, R. Moshenberg, R. Ghirlando and E. J. Wachtel in *Advanced Materials*, 3, 5, 251–254 (1991); which is incorporated herein by reference.

The dibenzopyrenes are generally prepared via sequential reactions involving (A) reaction of tetrachloro-1,4-benzoquinone with 3,3',4,4'-tetramethoxybiphenyl in 70% (v/v) aqueous sulfuric acid by shaking the reactants for 3 hours followed by reaction for one week at room temperature out of contact with moisture to provide 2,5,6,9,12,13-hexamethoxydibenzo[fg,op]naphthacene-1,8-quinone, followed by (B) grinding of the naphthacene-1,8-quinone with sodium dithionite acetone and water until the purple color disappears, followed by (C) demethylation of the isolated product from (B) via reaction with boron tribromide in dry benzene for 3 hours at reflux under a nitrogen atmosphere. The resulting 1,2,5,6,8,9,12,13-octahydroxydibenzo[fg, op]naphthacene can then be partially acetylated or O-alkylated. Alternately, the 2,5,6,9,12,13-hexamethoxydibenzo[fg,op]naphthacene-1,8-quinone can be demethylated, then O-alkylated to provide relatively long aliphatic hydrocarbon chains, followed by reduction with sodium dithionite to provide the 2,5,6,9,12,13-hexaalkoxy-1,8-dihydroxydibenzo[fg, op]naphthacene.

Methods for the synthesis of the dibenzopyrenes are taught by O. C. Musgrave and C. J. Webster, *J. Chem. Soc.(C)*, 1393–1397 (1971).

The tungsten-oxocalix[4]arenes are generally prepared via reaction of the calix[4]arene with a toluene or benzene solution of $WOCl_4$ at reflux for twelve hours. Alternately, reaction of the calix[4]arene with a benzene solution of $WCl_6$ at room temperature for 12 hours provides the calix [4]areneWCl$_2$ which is then refluxed in acetic acid in the presence of $AlCl_3$ for 24 hours to provide the corresponding tungsten-oxocalix[4]arene.

Methods for the synthesis of the tungsten-oxocalix[4] arenes are taught by F. Corazza, C. Floriani, A. Chiesi-Villa and C. Guastini, *J. Chem. Soc., Chem. Commun.*, 640–641 (1990); F. Corazza, C. Floriani, A. Chiesi-Villa and C. Rizzoli, *Inorg. Chem.*, 30, 4465–4468 (1991) and B. Xu and T. M. Swager, *J. Am. Chem. Soc.*, 115, 1159–1160 (1993); all of which are incorporated herein by reference.

The cis,cis-(3,5-dihydroxycyclohexyl)-3,4,5-tri (substituted)benzoates are generally prepared by reaction of cis,cis-1,3,5-cyclohexanetriol with phenyl boronic acid to provide 3-phenyl-2,4-dioxa-3-bora-bicyclo[3.3.1]nonan-7-ol which is then dissolved in pyridine and reacted with a 3,4,5-tri(substituted)benzoic acid chloride. Deprotection reaction of the resulting benzoate is completed in $H_2O_2$ (30%) and tetrahydrofuran to free the 3- and 5-hydroxy substituents.

Methods for the synthesis of the cis,cis-(3,5-dihydroxycyclohexyl)-3,4,5-tri(substituted)benzoates are taught by G. Lattermann and G. Staufer, *Liquid Crystals*, 10, 2, 169–183 (1991); G. Lattermann and G. Staufer, *Liquid Crystals*, 4, 4, 347–355 (1989) and M. Ebert, R. Kleppinger, M. Soliman, M. Wolf, J. H. Wendorff, G. Lattermann and G. Staufer, *Liquid Crystals*, 7, 4, 553–570 (1990); all of which are incorporated herein by reference.

DISCOTIC MESOGENIC MONOEPOXIDE COMPOUNDS, MONOTHIIANE COMPOUNDS, EPOXY RESINS AND POLYTHIIRANE RESINS

Suitable epoxy resins, polythiirane resins, monoepoxide compounds and monothiirane compounds containing one or more discotic mesogens or mesogenic moieties which are representative of the present invention include those represented by the Formulas VII, VIII, IX, X, XI and XII Formula VII $(M-Z^3)_p-D$ Formula VIII $(M-Z^3)_p{}^1-D-[(Q_n-R^1)_m{}^1-Q_n-R]_m$ Formula IX D—[(Q$_n$—R$^1$)$_m$$^1$—Q$_n$—Ar—Z$^3$—M]$_p$ Formula X (M—Z$^3$)$_p$$^1$—D—[(Q$_n$—R$^1$)$_m$$^1$—Q$_n$—Ar—Z$^3$—M]$_m$ Formula XI D—[(Q$_n$—R$^1$)$_m$$^1$—(Q$_n$—Ar)$_n$—Q$_n$—Z$^4$]$_p$ Formula XII (Z$^4$—Q$_n$)$_p$$^1$—D—[(Q$_n$—R$^1$)$_m$$^1$—Q$_n$—R]$_m$ wherein p, D, p$^1$, Q, n, R$^1$, R$^a$, m$^1$, m, Ar and R are as hereinbefore defined; each M is independently a

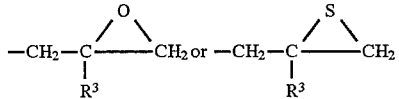

group; R$^3$ is hydrogen or a monovalent hydrocarbyl group having one to about 3 carbon atoms; each Z$^3$ is independently (a) a —O—, —S—, —NR—, —N<, or —CO—O— group where the single bonded oxygen atom attached to the carbon atom of —CO—O— is attached to the group represented by M, or (b) a —O—(CHR$^a$—CHR$^a$—O)$_p$$^3$—, or —CO—O—(CHR$^a$—CHR$^a$—O)$_p$$^3$—, —S—(CHR$^a$—CHR$^a$—O)$_p$$^3$—, —NR—(CHR$^a$—CHR$^a$—O)$_p$$^3$—, —N—((CHR$^a$—CHR$^a$—O)$_p$$^3$—)$_2$ group where the single bonded oxygen atom is attached to the group represented by M, Z$^4$ is an epoxidized olefinically unsaturated group having from 2 to about 20, preferably from about 10 to about 2, more preferably from about 4 to about 2 carbon atoms; p$^3$ has a value of one to about 100, preferably from about one to about 51, more preferably from about one to about 11; with the proviso the sum of p$^1$ and m in Formulas VIII, X, or XII must have a value of at least 3 or more.

Representative discotic mesogenic epoxy resins and monoepoxide compounds of Formulas VII, VIII, IX and X include, for example, mono and polyglycidyl ethers, mono and polymethylglycidyl ethers, mono and polyglycidyl esters, mono and polymethylglycidyl esters, mono and polyglycidyl amines, mono and polymethylglycidyl amines, mono and polythioglycidyl ethers, and mono and polymethylthioglycidyl ethers of the respective aforementioned discotic mesogenic compounds represented by Formulas I, II, III and IV. Additional representative discotic mesogenic epoxy resins and monoepoxide compounds include mono and polyglycidyl ethers of mono and poly(hydroxyalkylether)s or (hydroxyalkylpolyether)s, mono and polyglycidylether esters of mono and poly(hydroxyalkylester)s or mono and poly(hydroxyalkylpolyetherester)s, mono and polyglycidylether thioethers of mono and poly(hydroxyalkylthioether)s or mono and poly(hydroxyalkylpolyetherthioether)s, and mono and polyglycidylether amines of mono and poly(hydroxyalkylamine)s or mono and poly(hydroxyalkylpolyetheramine)s of the respective aforementioned discotic mesogenic compounds represented by Formulas I, II, III and IV. Representative discotic mesogenic polythiirane resins and monothiirane compounds include the thiiranes corresponding to each of the aforementioned epoxy resins and monoepoxide compounds. Representative discotic mesogenic epoxy resins and monoepoxide compounds of Formulas XI and XII include, for example, mono and polyglycidyl ethers, of the respective aforementioned discotic mesogenic compounds represented by Formulas V and VI.

Epoxidation of the discotic mesogenic compounds used to prepare the monoepoxide compounds and epoxy resins of the present invention can be performed by the known methods described in *Handbook of Epoxy Resins* by Lee and Neville, McGraw-Hill, (1967); Japan Kokai Tokkyo Koho JP 62 86,484(87 96,484); EP 88-008458/92 and *Journal of Applied Polymer Science*, vol. 23, 1355–1372 (1972); all of which are incorporated herein by reference. Generally, the respective hydroxyl, thiol, carboxylic acid or amine hydrogen containing compound is reacted with an excess of an epihalohydrin, such as, for example, epichlorohydrin or methyl epichlorohydrin, in the presence or absence of a suitable catalyst and in the presence or absence of a suitable solvent, at a temperature from about 0° C. to about 100° C., more suitably from about 20° C. to about 80° C., most suitably from about 20° C. to about 65° C. and at pressures suitably from about 30 mm Hg vacuum to about 100 psia (7.0307 kg/cm$^2$), more suitably from about 30 mm Hg vacuum to about 50 psia (3.5154 kg/cm$^2$), most suitably from about 60 mm Hg to about 20 psia (1.4061 kg/cm$^2$) and for a time sufficient to complete the reaction, usually from about 1 hour to about 1 week, more usually from about 1 hour to about 12 hours, most usually from about 1 hour to about 3 hours. This initial reaction unless the catalyst, is an alkali metal or alkaline earth metal hydroxide employed in stoichiometric quantities produces a halohydrin intermediate which is then dehydrohalogenated via reaction with a basic acting compound to convert the vicinal halohydrin groups to epoxide groups. The resultant product is the monoepoxide compound or epoxy resin.

For the production of monoepoxide compounds or epoxy resins from discotic mesogenic compounds possessing functional groups or linkages that are sensitive to hydrolysis under the reaction conditions employed in certain epoxidation chemistries, alternate techniques of preparation may be employed. As an example, Dhein, et al. in U.S. Pat. No. 4,762,901 teaches the preparation of the diglycidyl ether of 4'-hydroxyphenyl-4-hydroxybenzoate, which is a compound containing an ester linkage sensitive to hydrolysis, using an anhydrous epoxidation technique. This technique employs azeotropic removal of water/epichlorohydrin concurrent with the controlled addition of aqueous sodium hydroxide to a reaction mixture consisting of epichlorohydrin, a diphenol, a phase transfer catalyst such as, for example, tetra-n-butylammonium bromide, and, optionally, solvent(s). It is advantageous to conduct such anhydrous epoxidation reactions under a vacuum to facilitate the azeotropic removal of water. The azeotropic removal of water is usually conducted at temperatures of from about 20° C. to about 100° C., preferably from about 30° C. to about 65° C. It is also operable and advantageous to utilize the sodium hydroxide free of water as the alkali metal hydroxide reactant. In order to control reaction exotherm, the solid sodium hydroxide is typically added in aliquots as a powder to the epoxidation reaction mixture. A typical anhydrous epoxidation technique is described by Wang, et al. in U.S. Pat. No. 4,499,255 which is incorporated herein by reference in its entirety.

Another specific anhydrous epoxidation technique involves catalytic coupling of a hydroxyl, thiol, carboxylic acid or amine hydrogen containing compound with an epihalohydrin, typically using as a catalyst a phosphonium or ammonium halide at temperatures of from about 0° C. to about 100° C., preferably from about 20° C. to about 80° C., more preferably from about 50° C. to about 70° C., for a time sufficient to complete the reaction, usually from about 1 hour to about 1 week, preferably from about 4 hours to about 3 days, more preferably from about 6 hours to about 24 hours. The resultant solution of halohydrin in excess epihalohydrin is then treated with finely pulverized potassium carbonate to effect dehydrohalogenation to the monoepoxide compound or epoxy resin.

Suitable epihalohydrins which can be employed to prepare the monoepoxide compounds and the epoxy resins of the present invention include, for example, those represented by the following Formula XIII

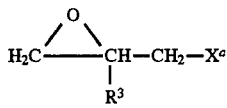

Formula XIII wherein $R^3$ is as previously defined and $X^a$ is a halogen. Particularly suitable such epihalohydrins include, for example, epichlorohydrin, epibromohydrin, epiiodohydrin, methylepichlorohydrin, methylepibromohydrin, methylepiiodohydrin, any combination thereof and the like.

Suitable catalysts which can be employed to prepare the monoepoxide compounds and epoxy resins of the present invention include, for example, quaternary ammonium compounds, phosphonium compounds, tertiary amines, and the like. Particularly suitable catalysts include, for example, benzyltrimethylammonium chloride, benzyltrimethylammonium bromide, tetra-n-butylammonium chloride, tetra-n-butylammonium bromide, tetra-n-octylammonium chloride, tetra-n-octylammonium bromide, tetramethylammonium chloride, tetramethylammonium bromide, tetramethylammonium hydroxide, ethyltriphenylphosphonium chloride, ethyltriphenylphosphonium bromide, ethyltriphenylphosphonium acetateoacetic acid complex, ethyltriphenylphosphoniumphosphate, tetra-n-butylphosphonium chloride, tetra-n-butylphosphonium bromide, tetra-n-butylphosphonium acetateoacetic acid complex, n-butyltriphenylphosphonium bisphenate, n-butyltriphenylphosphonium bicarbonate, triethylamine, tributylamine, any combination thereof and the like.

Suitable basic acting compounds which can be employed to prepare the monoepoxide compounds and epoxy resins of the present invention include, for example, alkali metal or alkaline earth metal hydroxides, carbonates, bicarbonates and the like. Particularly suitable such compounds include, for example, sodium hydroxide, potassium hydroxide, lithium hydroxide, calcium hydroxide, barium hydroxide, magnesium hydroxide, manganese hydroxide, sodium carbonate, potassium carbonate, lithium carbonate, calcium carbonate, barium carbonate, magnesium carbonate, manganese carbonate, sodium bicarbonate, potassium bicarbonate, lithium bicarbonate, calcium bicarbonate, barium bicarbonate, magnesium bicarbonate, manganese bicarbonate, any combination thereof and the like. Most preferred is sodium hydroxide or potassium hydroxide.

Suitable solvents which can be employed herein include, for example, alcohols, aliphatic hydrocarbohs, aromatic hydrocarbons, glycol ethers, amides, sulfoxides, sulfones, any combination thereof and the like. Particularly suitable solvents include, for example, methanol, ethanol, isopropanol, hexane, heptane, octane, nonane, decane, toluene, xylene, ethylene glycol methyl ether, ethylene glycol ethyl ether, ethylene glycol n-butyl ether, ethylene glycol phenyl ether, propylene glycol methyl ether, propylene glycol phenyl ether, tripropylene glycol methyl ether, diethylene glycol methyl ether, diethylene glycol ethyl ether, diethylene glycol n-butyl ether, diethylene glycol phenyl ether, butylene glycol methyl ether, N,N-dimethylformamide, N-methylpyrrolidinone, N,N-dimethylacetamide, dimethylsulfoxide, sulfolane, any combination thereof and the like.

If solvent is employed, it is usually employed in amounts suitably from about 5 to about 95, more suitably from about 20 to about 60, most suitably from about 30 to about 40, percent by weight based upon the combined weight solvent and epihalohydrin.

Epoxidation of the discotic mesogenic compounds containing an epoxidizable olefinically unsaturated group, such as, for example, the discotic mesogenic compounds represented by Formulas XI and XII can be performed using a variety of methods well known to the skilled artisan. Typical of these methods includes conversion of the olefin-containing precursor to a chlorohydrin via treatment with hypochlorous acid followed by dehydrochlorination of the resultant chlorohydrin intermediate thus formed; treatment of the olefin precursor with one or more organic peracids (Prilezhaev Reaction) or peracid forming compounds such as, for example, perbenzoic acid, m-chloroperbenzoic acid, acetaldehyde monoperacetate, monoperphthalic acid, peracetic acid, performic acid, trifluoroperacetic acid and 3,5-dinitroperoxybenzoic acid; or treatment of the olefin precursor with one or more inorganic peracids such as, for example, pertungstic acid. The peroxidation reaction is usually conducted at temperatures of from about 0° C. to about 100° C., preferably from about 20° C. to about 90° C., more preferably from about 25° C. to about 75° C.; or a time sufficient to complete the reaction, usually from about 5 minutes to about 24 hours, preferably from about 15 minutes to about 8 hours, more preferably from about 15 minutes to about 4 hours. Details concerning these methods are taught by the aformentioned *Handbook of Epoxy Resins*, pages 3-1 to 3-24 (1967); D. Swern in *Organic Reactions*, volume 7, pages 378–433 (1953) published by John Wiley and Sons, Inc.; D. Swern in *Organic Peroxides*, volume 2, pages 355–533 (1971) published by Wiley-Interscience; W. D. Emmons and A. S. Pagano, *Journal of the American Chemical Society*, 77, 89–92 (1955) and W. H. Rastetter, T. J. Richard and M. D. Lewis, *Journal or Organic Chemistry*, 43, 3163–3169 (1978); all of which are incorporated herein by reference. Additional methods for epoxidizing the olefinically unsaturated group involve reaction of the olefin precursor with oxygen or an alkyl peroxide either directly or in the presence of a catalyst consisting of a complex of vanadium, titanium, cobalt or molybdenum. Details concerning these methods are taught by T. Katsuki and K. B. Sharpless, *Journal of the American Chemical Society*, 102, 5974–5976 (1980); B. E. Rossiter, T. Katsuki and K. B. Sharpless, ibid., 103, 464–465 (1981); E. D. Mihelich, K. Daniels and D. J. Eickhoff, ibid., 103, 7690–7692 (1981); E. S. Gould, R. R. Hallet and K. C. Irwin, ibid., 90, 4573–4579 (1960); H. J. Ledon, P. Durbut and F. Varescon, ibid., 103, 3601–3603 (1981); L. D.-L. Lu, R. A. Johnson, M. G. Finn and B. K. Sharpless, *Journal of Organic Chemistry*, 49, 728–731 (1984) and R. A. Budnik and J. K. Kochi, ibid., 41, 1384–1389 (1976). As will be recognized by the skilled artisan, a wide range of additional olefin epoxidation techniques are available, notably the use of chromyl complexes in direct olefin epoxidation as taught by N. Miyaura and J. K. Kochi, *Journal of the American Chemical Society*, 105, 2368–2378 (1983); the use of a peroxysulfur intermediate in olefin epoxidation as taught by Y. H. Kim and B. C. Chung, *Journal of Organic Chemistry*, 48, 1562–1564 (1983); the use of tungstate plus phosphate (arsenate) ions with hydrogen peroxide to epoxidize olefins as taught by C. Venturello, E. Alneri and M. Ricci, ibid., 48, 3831–3833 (1983); the use of ferric chloride activated hydrogen peroxide in olefin epoxidation as taught by H. Sugimoto and D. T. Sawyer, ibid., 50, 1784–1786 (1985) and olefin epoxidation using sodium hypochlorite and tetraphenylporphrinatomanganese acetate as taught by M. E. DeCarvalho and B. Meunier, *Tetrahedron Letters*, 24, 3621–3624 (1983). The aforementioned references are incorporated herein by reference.

DISCOTIC MESOGENIC MONOTHIIRANE COMPOUNDS AND POLYTHIIRANE RESINS

The discotic mesogenic monoepoxide compounds and epoxy resins of the present invention can be converted to the monothiirane compounds and polythiirane resins containing one or more discotic mesogenic moieties via reaction of the epoxide group(s) therein with suitable sulfur containing compounds such as, for example, inorganic thiocyanates, thioureas, N-alkylbenzothiazol-2-thiones such as N-methylbenzothiazol-2-thione/trifluoroacetic acid or a phosphine sulfide such as triphenylphosphine sulfide/trifluoroacetic acid. Thus, typical of the monothiirane compounds and thiirane resins which contain one or more discotic mesogens or moieties are those represented by the aforementioned Formulas VII, VIII, IX, X, XI and XII, wherein Ar, D, Q, R, $R^1$, $R^3$, $R^a$, $Z^3$, n, m, $m^1$, p, $p^1$, and $p^3$ are as hereinbefore defined and M is a

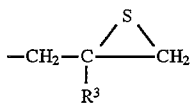

group.

Reaction conditions for the conversion of the epoxide group to the thiirane group are given by Bell and Ku in the article "Epoxy/Episulfide Resins", pages 3–26 and by Vecera and Spacek in the article "Preparation and Reactivity of Thiiranes", pages 73–80 both published in *Crosslinked Epoxies*, Sedlacek and Kahwec (editors), by Walter de Gruyter, New York (1987); Chan and Finkenbine, *Journal of the American Chemical Society*, 94, 2880 (1972); Calo, Lopez, Marchese and Pesce, *Journal of the American Chemical Society, Chemical Communications*, 621 (1975) and Hefner, Jr. and Earls in copending U.S. patent application Ser. No. 07/594,243 filed Oct. 9, 1990, all of which are incorporated herein by reference.

The reaction is usually conducted at temperatures of from about 5° C. to about 100° C., preferably from about 20° C. to about 60° C., for a time sufficient to complete the reaction, usually from about one hour to about 72 hours, preferably from about 4 hours to about 24 hours. The higher reaction temperatures typically require shorter times whereas the lower reaction temperatures typically require longer times to complete the reaction.

DISCOTIC MESOGENIC MONOEPOXIDE AND MONOTHIIRANE COMPOUNDS AS REACTIVE

The discotic mesogenic monoepoxide and monothiirane compounds of the present invention can be employed as reactive diluents for the discotic mesogenic epoxy and polythiirane resins. Said monoepoxide and monothiirane compounds are employed in amounts which provide the composition with the desired viscosity and reactivity profile desired for the particular purpose for which the composition is being employed. Usually the amount of monoepoxide or monothiirane compound is from about 1 to about 99, preferably from about 5 to about 40, percent by weight of all the compounds and resins containing epoxide and/or thiirane groups.

EPOXY RESINS

The discotic mesogenic monoepoxide compounds, discotic mesogenic monothiirane compounds, discotic mesogenic epoxy resins and discotic mesogenic polythiirane resins of the present invention can also be employed for the purpose of improving the properties of epoxy resins which do not contain one or more mesogenic discotic moieties or polythiirane resins which do not contain one or more mesogenic discotic moieties. Generally, the amounts of the discotic mesogenic monoepoxide or discotic mesogenic monothiirane compounds or the discotic mesogenic epoxy resins or discotic mesogenic polythiirane resins which are employed in combination with the compounds and resins which are free of discotic mesogenic moieties are from about one to about 99, more suitably from about 5 to about 80, most suitably from about 10 to about 55 weight percent of the discotic mesogen-containing compounds or resins based on the total weight of the combined resins and compounds.

Suitable epoxy resins which can be blended with the discotic mesogenic monoepoxide compounds, discotic mesogenic monothiirane compounds, discotic mesogenic epoxy resins and discotic mesogenic polythiirane resins include any compound containing an average of more than one vicinal epoxide group per molecule which does not contain discotic mesogenic moieties. Suitable such epoxy resins include, for example, aromatic polyepoxides, aliphatic polyepoxides, cycloaliphatic polyepoxides and the like. Particularly suitable epoxy resins include the diglycidyl ethers of: (a) compounds containing one or more aromatic rings and two or more aromatic hydroxyl groups per molecule, (b) compounds which are the result of reacting an alkylene oxide or monoglycidyl ether with the compounds of (a), (c) aliphatic diols which contain ether oxygen atoms or which are free of ether oxygen atoms, and (d) cycloaliphatic compounds containing more than one hydroxyl group per molecule.

Particularly suitable epoxy resins include, for example, (a) the diglycidyl ethers of o-, m-, p-dihydroxybenzene, bisphenol k (4,4'-isopropylidenediphenol), 4,4'-dihydroxydiphenylmethane, 4,4'-dihydroxybenzophenone, 3,3',5,5'-tetrabromobisphenol A, 4,4'-thiodiphenol, 4,4'-sulfonyldiphenol, 4,4'-dihydroxydiphenyl oxide, 1,1-bis(4-hydroxyphenyl)-1-phenylethane, 3,3',5,5'-tetrachlorobisphenol A, 3,3'-dimethoxybisphenol, 4,4'-dihydroxy-a-methylstilbene, 4,4'-dihydroxybenzanilide, 4,4'-dihydroxyazoxybenzene, 4,4'-dihydroxybiphenyl; (b) the triglycidyl ether of tris(hydroxyphenyl)methane; (c) the polyglycidyl ether of a phenol or alkyl or halogen substituted phenolaldehyde acid catalyzed condensation product (novolac resins), the polyglycidyl ether of a dicyclopentadiene or an oligomer thereof and a phenol or alkyl or halogen substituted phenol; (d) the advancement reaction products of the aforesaid di- and polyglycidyl ethers with aromatic dihydroxyl, containing compounds, aromatic polyhydroxyl containing compounds, dicarboxylic acid containing compounds, polycarboxylic acid containing compounds or a mixture therof, including, for example, bisphenol A, o-, m-, p-dihydroxybenzene, 2,4-dimethylresorcinol, 4,4'-dihydroxybiphenyl, 4,4'-dihydroxy-a-methylstilbene, 4,4'-dihydroxybenzanilide, 4-chlororesorcinol, tetramethylhydroquinone, 1,1-bis(4-hydroxyphenyl)ethane, 1,1-bis(4-hydroxyphenyl)-1-phenylethane, 4,4'-dihydroxydiphenyl ether, 3,3'5,5'-tetramethyl-4,4'-dihydroxydiphenyl ether, 3,3',5,5'-tetrachloro-4,4'-dihydroxydiphenyl ether, 4,4'-bis-(p-hydroxyphenylisopropyl)diphenyl ether, 4,4'-bis(4-hydroxyphenoxy)benzene, 4,4'-bis(4-hydroxyphenoxy) diphenyl ether, 4,4'-bis(4(4-hydroxyphenoxy) phenylsulfone)diphenyl ether, 4,4'-dihydroxydiphenyl sulfone, 4,4'-dihydroxydiphenyl sulfone, 4,4'-dihydroxydiphenyl sulfide, 4,4'-dihydroxydiphenyldisulfide, 2,2'-dihydroxydiphenyl sulfone, 4,4'-dihydroxydiphenyl methane, 1,1'-bis(4-hydroxyphenyl)cyclohexane, 4,4'-dihydroxybenzophenone, phloroglucinol, pyrogallol, 2,2',5,5'-tetrahydroxydiphenyl sulfone, tris(hydroxyphenyl)

methane, dicyclopentadiene diphenol, tricyclopentadiene diphenol, 4,4'-dicarboxydiphenyl ether, 1,6-hexanedicarboxylic acid; and (e) any combination of the aforementioned epoxy resins and the like.

DISCOTIC MESOGENIC VINYL ESTER RESINS

The discotic mesogenic monoepoxide compounds and epoxy resins of the present invention may be converted to the monovinyl ester compounds and vinyl ester resins containing one or more discotic mesogens or mesogenic moieties via reaction of the epoxide group(s) therein with one or more polymerizable monounsaturated monocarboxylic acids. The resultant vinyl esters all contain the characteristic linkage

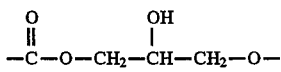

and terminal vinyl or vinylidene groups. Thus, typical of the vinyl ester resins and monovinyl ester compounds which contain one or more discotic mesogenic moieties are those represented by the aforementioned Formulas VII, VIII, IX, X, XI and XII, wherein Ar, D, Q, R, $R^1$, $R^3$, $R^a$, $Z^3$, m, $m^1$, n, p, $p^1$, and $p^3$ are as hereinbefore defined and M is a

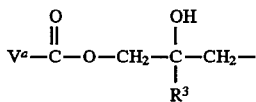

group wherein $V^a$ is a vinyl or vinylidene group.

Suitable polymerizable monounsaturated monocarboxylic acids for reaction with the discotic mesogenic monoepoxide compounds and epoxy resins include, for example, acrylic acid, methacrylic acid, cyanoacrylic acid, a-phenylacrylic acid, methoxyacrylic acid, cinnamic acid, crotonic acid, monomethylester of maleic acid, monomethylester of fumaric acid, monomethylester of itaconic acid, mixtures thereof and the like. Methacrylic acid is a most preferred polymerizable monounsaturated monocarboxylic acid. A mole ratio of 0.7 to 1.2 polymerizable monounsaturated monocarboxylic acid per epoxide group is preferred, with a mole ratio of 0.95 to 1.0 being most preferred.

The reaction between the epoxide group and the carboxylic acid group is typically performed in the presence of one or more catalysts. Chromium trichloride, tris (dimethylaminoethyl)phenol and ethyltriphenylphosphonium acetate-acetic acid complex are most preferred as the catalysts. A quantity of from about 0.01 to about 2 weight percent of the total reactants used has been found to be a particularly suitable quantity of catalyst with concentrations of about 0.1 to about 0.3 weight percent of the total reactants used being most preferred.

A suitable process inhibitor is typically used in the reaction between the epoxide group and the carboxylic acid group to prevent gelation (homopolymerization of the vinyl ester, and/or copolymerization of the vinyl ester with unreacted monounsaturated monocarboxylic acid). Hydroquinone activated with air is a most preferred inhibitor at concentrations of from about 100 ppm to about 500 ppm based on the weight of the total reactants used.

The reaction to produce the discotic mesogenic monovinyl ester compounds and vinyl ester resins is optionally conducted in one or more organic solvents inert to the other reactants. The term "inert" means that little, if any, reaction between the monoepoxide compound and/or epoxy resin, the polymerizable monounsaturated monocarboxylic acid, or the vinyl esters thereof occurs under the reaction conditions employed. Typical of the inert organic solvents are the aliphatic ketones, such as methylisobutyl ketone, the chlorinated aliphatic compounds, such as perchloroethylene, the aromatic hydrocarbons, such as toluene, and the aliphatic ethers, such as 1,4-dioxane.

The reaction to produce the discotic mesogenic monovinyl ester compounds and vinyl ester resins is usually conducted at a temperature of from about 50° C. to about 125° C., preferably from about 80° C. to about 120° C., for from about 90 minutes to about 720 minutes, preferably from about 120 minutes to about 420 minutes. Although reaction times and reaction temperatures can vary substantially, most preferred vinyl ester compositions are produced by reacting to a specific conversion, typically 1.5 to 0.25 percent carboxylic acid.

The discotic mesogenic vinyl ester resin is typically combined with one or more polymerizable ethylenically unsaturated monomers. The vinyl ester resin and polymerizable ethylenically unsaturated monomer blend can consist of from 1 to 99, preferably from about 20 to about 80, most preferably from about 30 to about 70 percent by weight of one or more polymerizable ethylenically unsaturated monomers with the balance of the combined weight consisting of said vinyl ester resin(s).

Suitable polymerizable ethylenically unsaturated monomers which can be employed herein can be selected from the many known classes of polymerizable ethylenically unsaturated monomers. Representatives of such monomers include, for example, the vinyl aromatic compounds such as styrene, vinylnaphthalenes, a-methylstyrene, o-, m-, p-vinyltoluenes, o-, m-, p-halostyrenes, o-, m-, p-tertiary-butylstyrenes, o-, m-, p-divinylbenzenes, any combination thereof and the like. Other suitable monomers include the methyl, ethyl, isopropyl, octyl, esters of acrylic and methacrylic acid; the hydroxyalkyl esters of acrylic and methacrylic acid; acidic monomers such as acrylic acid, methacrylic acid and crotonic acid; amide monomers such as acrylamide and N-alkylacrylamides; allyl monomers such as diallylphthalate, triallyisocyanurate, diallylmaleate and dimethallylfumarate; any combination thereof and the like.

In a preferred process of the present invention, one or more epoxy resins which do not contain discotic mesogens or mesogenic moieties and one or more monoepoxide compounds containing at least one discotic mesogenic moiety are simultaneously reacted with one or more polymerizable monounsaturated monocarboxylic acids to provide a mixture containing both the vinyl ester of the epoxy resin and the monovinyl ester of the monoepoxide compound. In this manner, a thermosettable vinyl ester resin mixture containing discotic mesogenic functionality is produced wherein said discotic mesogenic moiety is only present as a side chain moiety (pendant from the polymerizable monovinyl group derived from the monoepoxide compound). Likewise, if both the epoxy resin and monoepoxide compound contain at least one discotic mesogenic moiety, a thermosettable vinyl ester resin mixture containing discotic mesogenic functionality is produced wherein said discotic mesogenic moieties are present both as a main chain moiety (in the backbone of the vinyl ester molecules derived from the epoxy resin) and as a side chain moiety (pendant from the polymerizable monovinyl group derived from the monoepoxide compound). Vinyl ester resin mixtures containing discotic mesogenic moieties present only as main chain moieties can additionally be produced.

CURING AGENTS FOR DISCOTIC MESOGENIC EPOXY AND POLYTHIIRANE RESINS

The compositions of the present invention containing an average of more than one vicinal epoxide group and at least one discotic mesogenic moiety per molecule or more than one vicinal thiirane group and at least one discotic mesogenic moiety per molecule can be cured with any suitable curing agent or catalyst for curing epoxy or polythiirane resins. Typical such curing agents include, for example, aliphatic, cycloaliphatic or aromatic primary monoamines, aliphatic, cycloaliphatic or aromatic primary and secondary polyamines, carboxylic acids and anhydrides thereof, aromatic hydroxyl containing compounds, imidazoles, guanidines, urea-aldehyde resins, melamine-aldehyde resins, alkoxylated urea-aldehyde resins, alkoxylated melamine-aldehyde resins, combinations thereof and the like. Particularly suitable curing agents and catalysts include, for example, methylene dianiline, dicyandiamide, ethylene diamine, diethylenetriamine, triethylenetetramine, tetraethylenepentamine, urea-formaldehyde resins, melamine-formaldehyde resins, methylolated urea-formaldehyde resins, methylolated melamine-formaldehyde resins, phenol-formaldehyde novolac resins, cresol-formaldehyde novolac resins, sulfanilamide, diaminodiphenylsulfone, diethyltoluenediamine, t-butyltoluenediamine, bis-4-aminocyclohexylamine, isophoronediamine, diaminocyclohexane, hexamethylenediamine, piperazine, aminoethylpiperazine, 2,5-dimethyl-2,5-hexanediamine, 1,12-dodecanediamine, tris-3-aminopropylamine, combinations thereof and the like.

Typical such curing catalysts include, for example, boron trifluoride, boron trifluoride etherate, aluminum chloride, ferric chloride, zinc chloride, silicon tetrachloride, stannic chloride, titanium tetrachloride, antimony trichloride, boron trifluoride monoethylamine complex, boron trifluoride triethanolamine complex, boron trifluoride piperidine complex, pyridine-borane complex, diethanolamine borate, zinc fluoroborate, mixtures thereof and the like.

Especially preferred as the curing agent are the discotic mesogenic compounds containing an average of more than one hydrogen reactive with an epoxide group and which are precursors to the discotic mesogenic epoxy resins. Representative of such curing agents are the aformentioned discotic mesogenic compounds of Formulas I, II, III and IV wherein p, $p^1$, p and $p^1$, respectively, have a value of greater than one.

The curing agents are employed in amounts which will effectively cure the composition, however, these amounts will depend upon the particular discotic mesogenic epoxy or polythiirane resin employed and curing agent employed. Generally, suitable amounts include, for example, from about 0.80:1 to about 1.2:1 equivalents of curing agent per equivalent of epoxy or polythiirane resin.

The curing catalysts are employed in amounts which will effectively cure the composition, however, these amounts will depend upon the particular discotic mesogenic epoxy or polythiirane resin employed and curing agent employed. Generally, suitable amounts include, for example, from about 0.001 to about 2 percent by weight of the curing catalyst based on the total weight of polyepoxy or polythiirane resin used. It is frequently of benefit to employ one or more of the curing catalysts in conjunction with one or more curing agents in the curing of the discotic mesogenic epoxy and polythiirane resins of the present invention. This is generally done to accelerate or otherwise modify the curing behavior obtained when a curing agent or a curing catalyst is used singly.

The curing of the compositions of the present invention containing an average of more than one vicinal epoxide or thiirane group and at least one discotic mesogenic moiety per molecule can be conducted at atmospheric, superatmospheric or subatmospheric pressures at temperatures of from about 0° C. to about 300° C., preferably from about 50° C. to about 240° C., more preferably from about 100° C. to about 200° C. The time required to complete the curing depends upon the temperature employed. Higher temperatures require shorter periods of time whereas lower temperatures require longer periods of time. Generally, however, times of from about one minute to about 48 hours, preferably from about 15 minutes to about 8 hours, more preferably from about 30 minutes to about 3 hours are suitable. Depending on the relative phase transition temperature(s) associated with the discotic mesogenic moieties present in the epoxy resin or polythiirane resin compositions, curing at an elevated temperature can be especially desireable to enhance the molecular anisotropy of the cured product. It is frequently of value to B-stage the discotic mesogen-containing epoxy resin or polythiirane resin compositions in order to chain extend the resin. This chain extension is required for some discotic mesogen-containing epoxy or polythiirane resin compositions in order to achieve liquid crystal character. B-staging can also be employed to increase the temperature range at which a particular resin composition is liquid crystalline and to control the degree of crosslinking during the final curing stage.

The compositions of the present invention containing an average of one vicinal epoxide group and at least one discotic mesogenic moiety per molecule can be polymerized in the presence of one or more initiators selected from the group consisting of alcohols, diols and water using at least one curing catalyst selected from the group consisting of Lewis acids and protic acids. The resultant products are substantially linear polymers containing at least one terminal hydroxyl group and pendant (side chain) discotic moieties. Methods for the Lewis acid or protic acid catalyzed polymerization of monoepoxide compounds in the presence of an initiator are given by T. Biedron, P. Kubisa and S. Penczek, *Journal of Polymer Science: Part A: Polymer Chemistry*, volume 2, 619–628 (1991), which is incorporated herein by reference.

The compositions of the present invention containing the vinical thiirane group and at least one discotic mesogenic moiety per molecule can also be "self-cured", that is, subjected to heat, until reaction of the thiirane moieties occurs. It is felt that the self-curing results from initial opening of the thiirane ring to form a stable sulfide ion which subsequently anionically attacks another thiirane ring. It is frequently of benefit to partially (B-stage) or totally homopolymerize (self-cure) the polythiirane resins containing one or more discotic mesogenic moieties to produce resin compositions possessing discotic liquid crystalline character.

CURING OF THE DISCOTIC MESOGENIC VINYL ESTER RESINS

The curing of the discotic mesogenic vinyl ester compositions is effected by the application of heat and/or pressure in the presence of a free radical forming catalyst. Catalysts that can be employed for the curing are preferably the peroxide catalysts, such as benzoyl peroxide, lauroyl peroxide, t-butylhydroperoxide, methylethylketone peroxide, t-butylperbenzoate, potassium persulfate, mixtures thereof and the like. The amount of catalyst added will vary from 0.1 to about 2 percent by weight, preferably from 0.5 to 1.5 percent by weight. Temperatures employed can vary over a considerable range but usually are in the range of 20° C. to 250° C. Depending on the relative solubility and phase transition temperature(s) associated with the discotic mesogenic moieties present in the vinyl ester resin compositions, curing at an elevated temperature can be especially desireable to enhance the molecular anisotropy of the cured product.

Additionally, more rapid curing of the vinyl ester resin compositions can be accomplished by the addition of accelerating agents such as lead or cobalt naphthenate, N,N-dimethylaniline, mixtures thereof and the like, usually in concentrations ranging from about 0.01 to about 2 percent by weight, preferably 0.05 to 0.5 percent by weight.

ORIENTATION

During the processing and/or curing of the discotic mesogenic monoepoxide compounds, monothiirane compounds, epoxy resin compositions, polythiirane resin compositions or vinyl ester resin compositions, electric or magnetic fields or drawing and/or shear forces can be applied for the purpose of orienting or otherwise modifying the existing orientation of the discotic mesogenic moieties contained or developed therein which can in effect improve the mechanical properties. As a specific example of these methods Huser and Spiess, *Makromol. Chem., Rapid Commun.*, 9, 337–343 (1988) induced orientation in polymers containing the triphenylene discotic mesogen as evidenced by macroscopic alignment in high magnetic fields. Additional examples of orientation of discotic liquid crystalline monomers, oligomers and polymers in a magnetic field are given by Goldfarb, et al, *J. Phys. (Les Ulis, Fr.)*, 42, 1303 (1981). Mechanical forces, such as uniaxial stretching, induce orientation in main chain discotic liquid crystalline polymers as shown by Herrmann-Schonherr, et al, *Makromol. Chem., Rapid Commun.*,7, 97 (1986) and Huser, et al, *Macromolecules*, 22, 1960 (1989). It is highly desireable to align all columns in the discotic liquid crystalline matrix parallel to each other such that a monodomain is formed. This is usually accomplished by heating of the discotic liquid crystal sample above its isotropization temperature followed by slow cooling to below the isotropization temperature while simultaneously rotating around the sample axis, concurrent with the application of a magnetic field. Because crosslinking, as occurs in the curing (thermosetting) process, makes monodomain formation much more difficult, it is frequently of value to preform the monodomain at some step prior to or early in the crosslinking process.

Processing methods which induce drawing and/or shear forces include those processes where the polymeric mesophase flows through a die, orefice or mold gate. Thus injection molding, extrusion, pultrusion, filament winding, filming, prepregging, uniaxial and biaxial stretching or combinations of such processing methods can be used to induce and control orientation.

When the processing and/or curing of the discotic mesogenic monoepoxide compounds, monothiirane compounds, epoxy resin compositions, polythiirane resin compositions or vinyl ester resin compositions, is on a surface, such as, for example, in the preparation of a thin film coating, the surface can be modified for the purpose of orienting or otherwise modifying the existing orientation of the discotic mesogenic moieties contained or developed therein which can in effect improve the mechanical properties. As a specific example of these methods Vauchier, et al, *Mol. Cryst. Liq. Cryst.*, 66, 103 (1981) oriented hexasubstituted triphenylenes with alignment of the directors perpendicular to the walls on glass surfaces coated with flat molecules possessing six polar side-functions. For a material containing the $D_F$ mesophase, alignment with the directors parallel to the surfaces is obtained using glass surfaces coated with silicon oxides deposited at oblique incidence. Because crosslinking, as occurs in the curing (thermosetting) process, makes alignment of the discotic mesophase more difficult, it is frequently of value to preform the aligned discotic mesophase at some step prior to or early in the crosslinking process.

DOPANTS

One or more dopants may be added to the discotic mesogenic monoepoxide compounds, monothiirane compounds, epoxy resin compositions, polythiirane resin compositions or vinyl ester resin compositions for the purpose of inducing new functional behavior or to induce liquid crystallinity in non-liquid crystalline systems. This is accomplished via electron donor-acceptor interactions between disk-like core structures of the electron rich discotic compounds and low molecular weight electron acceptors. Typical low molecular weight electron acceptors include 2,4,7-trinitrofluorenone and 2,4,7-trinitro-9-fluorenylidenemalonodinitrile. As a specific example of these methods, Ringsdorf, et al, *Angew. Chem. Int. Ed. Engl.*, 28,7, 914–918 (1989) doped an amorphous polyester which contained triphenylene units in the main chain with 2,4,7-trinitrofluorenone resulting in the induction of the discotic mesophase.

Dopants consisting of a long chain derivative of a low molecular weight electron acceptor may be added to the discotic mesogenic monoepoxide compounds, monothiirane compounds, epoxy resin compositions, polythiirane resin compositions or vinyl ester resin compositions for the purpose of downgrading the discotic mesophase to the discotic nematic mesophase. A typical long chain derivative of a low molecular weight electron acceptor is (2,4,7-trinitro-9-fluorenylidene)malonic bis(hexadecylester). As a specific example, Bengs, et al, *Liquid Crystals*, 10, 2, 161–168 (1991) mixed the discotic hexagonal phase forming compound, hexakispentyloxytriphenylene, with (2,4,7-trinitro-9-fluorenylidene)malonic bis(hexadecylester) resulting in induction of the nematic columnar phase. The long chain of the electron acceptor was demonstrated to introduce strong assymetry into the electron donor (disk-like core structure)-acceptor complex. A key to this effect is the difference in chain length of the chains associated with the electron donor and the chain(s) of the electron acceptor which strongly influences packing behavior due to steric effects.

OTHER COMPONENTS

The discotic mesogenic monoepoxide compounds, monothiirane compounds, epoxy resin compositions, polythiirane resin compositions or vinyl ester resin compositions of the present invention can be blended with other materials such as solvents or diluents, fillers, pigments, dyes, flow modifiers, thickeners, reinforcing agents, mold release agents, wetting agents, stabilizers, fire retardant agents, surfactants, combinations thereof and the like.

These additives are added in functionally equivalent amounts, e.g., the pigments and/or dyes are added in quantities which will provide the composition with the desired color, however, they are suitably employed in amounts of from about zero to about 20, more suitably from about 0.5 to about 5, most suitably from about 0.5 to about 3 percent by weight based on the weight of the total blended composition.

Solvents or diluents which can be employed herein include, for example, hydrocarbons, chlorinated hydrocarbons, ketones, glycol ethers, aliphatic ethers, cyclic ethers, esters, amides, sulfoxides, sulfones, combinations thereof and the like. Particularly suitable solvents or diluents include, for example, toluene, benzene, xylene, methylethyl ketone, methylisobutyl ketone, methylamyl ketone, diethylene glycol methyl ether, dipropylene glycol methyl ether, propylene glycol methyl ether, dimethylformamide, N-methylpyrrolidinone, tetrahydrofuran, 1,4-dioxane, perchloroethylene, methylene chloride, dimethylsulfoxide, combinations thereof and the like.

The modifiers such as thickeners, flow modifiers and the like can suitably employed in amounts of from zero to about 10, more suitably from about 0.5 to about 6, most suitably from about 0.5 to about 4 percent by weight based on the weight of the total composition.

Reinforcing materials which can be employed herein include natural and synthetic fibers in the form of woven fabric, mats, monofilament, multifilament, unidirectional fibers, rovings, random fibers or filaments, inorganic fillers or whiskers, hollow spheres, and the like. Suitable reinforcing materials include glass, ceramics, nylon, rayon, cotton, aramid, graphite, polyalkylene terephthalates, polyethylene, polypropylene, polyesters, combinations thereof and the like.

Suitable fillers which can be employed herein include, for example, inorganic oxides, ceramic microspheres, plastic microspheres, glass microspheres, inorganic whiskers, $CaCO_3$, combinations thereof and the like.

The fillers can be employed in amounts suitably from about zero to about 95, more suitably from about 10 to about 80, most suitably from about 40 to about 60 percent by weight based upon the weight of the total composition.

The discotic mesogenic monoepoxide compounds, monothiirane compounds, epoxy resin compositions, polythiirane resin compositions or vinyl ester resin compositions of the present invention can be employed in coating, casting, encapsulation, electronic or structural laminate or composite, filament winding, molding and the like applications.

The following examples are illustrative of the present invention, but are not to be construed as to limiting its scope in any manner.

EXAMPLE 1

A. Synthesis of 2,3,6,7,10,11-Hexamethoxytriphenylene 1,2-Dimethoxybenzene (138.0 grams, 0.999 mole) and ferric chloride (81.2 grams, 0.501 mole) were added to a glass resin kettle reactor and stirred under a nitrogen atmosphere as a slurry. The slurry exotherms to a 70° C. temperature, then after stirring for 10 minutes, the temperature of the slurry was 65° C. After an additional 5 minutes, the temperature of the slurry was 55° C. and at this time, deionized water (9.0 grams, 0.5 mole) was added dropwise to the slurry over a 5 minute period. At the completion of the water addition, the reaction temperature was increased to 75° C. and held therein for the next 20 minutes. The resultant slurry was diluted with deionized water (250 milliliters) then filtered. The precipitate was recovered and was washed with ethanol (400 milliliters) followed by filtration. The precipitate was recovered and washed with 5N aqueous hydrochloric acid (400 milliliters) followed by filtration. The precipitate was recovered and washed with deionized water (400 milliters) followed by filtration. The precipitate was recovered and dried in a forced air, convection type oven for 16 hours at 50° C. to provide a dry purple colored powder. Portions of the powder were dissolved in chloroform then applied to a silca gel column and eluted with chloroform. A yellow colored product band elutes first and was retained, while a purple colored band was left on the column. The chloroform solvent was removed from the eluted solution of product by rotary evaporation to provide a pale creme colored powder. After drying to a constant weight, 7.53 grams of product was recovered. High pressure liquid chromatographic analysis reveals a single peak for the 2,3,6,7,10,11-hexamethoxytriphenylene product in excess of 95 area percent (detector at 254 nm), with a single minor coproduct peak present. Differential scanning calorimetry of a portion (10.1 or 12.3 milligrams) of the product using a heating rate of 10° C. per minute, and a range from 30° to 350° C. under a stream of nitrogen flowing at a rate of 35 cubic centimeters per minute reveals a sharp melting point endotherm with a minimum at 311° C. and an enthalpy of 136 joules per gram (data averaged from two analysis). Fourier transform infrared spectrophotometric analysis of a potassium bromide pellet of the product reveals the presence of the C—H stretch vibration for the aromatic ring at 3104 $cm^{-1}$, the C—H stretch vibration for the methoxy group at 2831 $cm^{-1}$, the C—H stretch vibrations for the aromatic ring C=C groups at 1623, 1523 and 1463 (1437 shoulder) $cm^{-1}$, the aromatic ring C—O vibration for the ether linkage at 1264 $cm^{-1}$, the aliphatic portion of the C—O vibration for the ether linkage at 1045 $cm^{-1}$, aromatic ring C—O stretch vibration at 1158 $cm^{-1}$ and the C—H out-of-plane vibration for the aromatic rings at 832 and 779 $cm^{-1}$.

B. Synthesis of 2,3,6,7,10,11-Hexahydroxytriphenylene

A portion (1.702 grams, 0.025 methoxy equivalent) of 2,3,6,7,10,11-hexamethoxytriphenylene from A above and benzene (250 milliliters) were added to a glass three necked round bottom reactor and stirred under a nitrogen atmosphere as a slurry. Boron tribromide (10.792 grams, 0.0431 mole) was added to the slurry, then heating commences until a reflux temperature of 82° C. was achieved. After 160 minutes at the 82° C. reflux, the nitrogen blanket was removed from the reactor and a distillation head was added. A vacuum was introduced to effect distillation of the benzene solvent plus any unreacted boron tribromide from the reactor. The resultant dry powder remaining in the reactor was combined with deionized water (400 milliliters), then stirred under a nitrogen atmosphere with heating to 100° C. The resultant slurry was cooled to 80° C., then filtered. The precipitate was recovered and was washed with deionized water (50 milliliters) followed by filtration. The recovered precipitate was dried in a vacuum oven at 25° C. and 1 mm Hg to a constant weight of 1.35 grams of pale gray colored product. High pressure liquid chromatographic analysis reveals a single peak for the 2,3,6,7,10,11-hexahydroxytriphenylene product at 95 area percent (detector at 254 nm), with a single minor coproduct peak present. Differential scanning calorimetry of a portion (9.1 or 12.8 milligrams) of the product using a heating rate of 10° C. per minute, and a range from 30° to 500° C. under a stream of nitrogen flowing at a rate of 35 cubic centimeters per minute reveals a sharp melting point endotherm with a minimum at 398.1° C. and an enthalpy of 27.0 joules per gram. A sharp exothermic rise above the baseline comprises the endpoint of this endotherm and was immediately followed by a sharp endothermic descent below the baseline, then a sharp exotherm with a maximum at 423.4° C. and an enthalpy of 99.0 joules per gram (data averaged from two analysis). Infrared spectrophotometric analysis of a potassium bromide pellet of the product reveals the disappearance of the C—H stretch vibration for the methoxy group at 2831 cm$^{-1}$, the aromatic ring C—O vibration for the ether linkage at 1264 cm$^{-1}$ and the aliphatic portion of the C—O vibration for the ether linkage at 1045 cm$^{-1}$, concurrent with the presence of the O—H stretch vibration for the phenolic hydroxyl group at 3422 (3296 slight shoulder) cm$^{-1}$, the C—H stretch vibrations for the aromatic ring C=C groups at 1629 (1603 shoulder), 1536 and 1443 cm$^{-1}$, aromatic ring C—O stretch vibrations at 1277, 1224 and 1178 cm$^{-1}$, O—H deformation at 1370 cm$^{-1}$ and the C—H out-of-plane vibration for the aromatic rings at 859 and 793 cm$^{-1}$.

C. Synthesis of 2,3,6,7,10,11-Hexaglycidyloxytriphenylene

A portion (1.284 grams, 0.02375 hydroxy equivalent) of 2,3,6,7,10,11-hexahydroxytriphenylene from B above, epichlorohydrin (439.6 grams, 4.751 moles) and tetrabutylammonium bromide (0.0128 gram, 1.0% wt. of the hexahydroxytriphenylene reactant used) were added to a glass three necked round bottom reactor and stirred under a nitrogen atmosphere as a solution. Heating commences until a temperature of 80° C. was achieved. After 5 days at the 80° C. temperature, the solution was recovered and rotary evaporated to provide a viscous, light amber colored, liquid. Titration of a portion of the product reveals the presence of 14.79% epoxide. The product was dissolved into 50/50 weight percent methylethylketone/toluene (200 milliliters) and the resultant solution was added to a three necked round bottom reactor and stirred under a nitrogen atmosphere. Sodium hydroxide (0.95 gram, 0.02375 mole) dissolved in deionized water (2 milliliters) was added to the reactor, then heating to 50° C. commences. This temperature was maintained for 3 hours followed by rotary evaportaion of the reaction slurry to dryness. The resultant product was dissolved in methylene chloride (150 milliliters), then extracted with deionized water (100 milliliters). The recovered methylene chloride solution was dried over anhydrous sodium sulfate then filtered and rotary evaporated to provide a constant weight of 3.01 grams of a tacky, light amber colored semi-solid product. Titration of a portion of this product reveals the presence of 24.64% epoxide. The crude epoxy resin was then dissolved in methylethylketone (20 mililiters) followed by addition of toluene (60 milliliters) inducing precipitation. The slurry was held at 25° C. for the next 16 hours, then the solvent was decanted from the crystalline precipitate and rotary evaporated to dryness. Acetone (5 milliliters) was added to the product then evaporated under a steam of nitrogen commences. Once the evaporation had left 3 milliliters of volume, extensive crystallization occcurs. This crystalline powder was recovered by filtration and dried in a vacuum oven at 25° C. and 1 mm Hg to a constant weight of 0.68 grams of crystalline white product. Titration of a portion of the product reveals the presence of 32.45% epoxide (132.65 epoxide equivalent weight). Infrared spectrophotometric analysis of a potassium bromide pellet of the product reveals the disappearance of the O—H stretch vibration for the phenolic hydroxyl group at 3422 (3296 slight shoulder) cm$^{-1}$ and the O—H deformation at 1370 cm$^{-1}$ concurrent with the presence of the C—H stretch vibration for the aromatic ring at 3064 cm$^{-1}$, the C—H stretch vibrations for the aromatic ring C=C groups at 1616, 1583 (weak), 1510 and 1430 cm$^{-1}$, the aromatic ring C—O vibration for the ether linkage at 1264 cm$^{-1}$ (masks the weak epoxide ring C—O stretch vibration expected at 1250 cm$^{-1}$), the aliphatic portion of the C—O vibration for the ether linkage at 1045 cm$^{-1}$, the aromatic ring C—O stretch vibration at 1171 cm$^{-1}$, the epoxide ring vibration at 912 cm$^{-1}$ and the C—H out-of-plane vibration for the aromatic rings at 848 (broadened due to overlap with epoxide ring vibration expected at 835 cm$^{-1}$) and 766 cm$^{-1}$. Mass spectroscopic analysis using electron impact ionization and the direct probe to introduce the sample reveals the expected molecular radical cation at a mass to charge ratio of 660 with the base peak at a mass to charge ratio of 57.

D. Characterization of 2,3,6,7,10,11-Hexaglycidyloxytriphenylene by Differential Scanning Calorimetry and Optical Microscopy Under Crosspolarized Light Differential scanning calorimetry of a portion (9.3 or 8.2 milligrams) of the product using a heating and cooling rate of 10° C. per minute, and a range from −50° to 250° C. for heating immediately followed by cooling from 250° to −50° C., under a stream of nitrogen flowing at a rate of 35 cubic centimeters per minute reveals a broad endotherm with a minimum at 46.5° C. and an enthalpy of 14.65 joules per gram, followed by a sharp endotherm with a minimum at 154.8° C. and an enthalpy of 23.6 joules per gram, then a sharp endotherm with a minimum at 178.5° C. and an enthalpy of 6.28 joules per gram (data averaged from two analysis). Optical microscopy under crosspolarized light was performed on the opaque, pale yellow colored, fused solid recovered from the differential scanning calorimetry and reveals a highly birefringent, columnar mesophase having a fine focal-conic texture with a starlike appearance.

Optical microscopy under crosspolarized light was performed at 70× magnification using a microscope equipped with a heated stage. A sample of the hexaglycidyloxytriphenylene was applied to a glass slide then covered with a glass coverslip and placed on the hot stage. Heating at a rate of 10° C. per minute commences with the following results obtained:

| Temperature (°C.) | Comments |
| --- | --- |
| 30 | Birefringent crystalline solid. |
| 158 | Softening noted when compressed between coverslip and glass slide, highly birefringent with fine grainy appearing texture. |
| 185 | Stir opalescent, highly birefringent viscous fluid with fine grainy appearing texture, flow only observed as compressed between coverslip and glass slide. |
| 200 | Same as at 185° C. |
| 215 | Birefringent fluid now flows without compressing the coverslip and glass slide. |

| Temperature (°C.) | Comments |
|---|---|
| 234 | Isotropization onsets. |
| 239 | Isotropization complete. |
| 245 | Beginning cooling of isotropic fluid (clear droplets when crosspolarization removed). |
| 223 | First highly birefringent cylinderical shaped spots appearing. |
| 217 | Spots have grown to a highly birefringent columnar mesophase having a focal-conic texture, highly viscous fluid that was mobile only when stirred or compressed between the coverslip and glass slide. Stirring causes the columnar mesophase to fracture apart and the birefringent fine grainy appearing textured fluid to reform. (Like the columnar mesophase pictured in Liquid Crystals, volume 7, number 2, February, 1990 on page 166 in FIG. 3 for 2,3,6,7,10,11-hexa-n-hexyloxytriphenylene.) |
| 155 | Birefringent solid forms (waxlike), fine grainy appearing texture present with particles of the columnar mesophase dispersed therein. |

EXAMPLE 2

Preparation and Characterization of a Curable Mixture and Cured Composition Thereof Based on 2,3,6,7,10,11-Hexaglycidyloxytriphenylene and 2,3, 6,7,10,11-Hexahydroxytriphenylene A portion (0.0238 gram, 0.000179 epoxide equivalent) of the 2,3,6,7,10,11-hexaglycidyloxytriphenylene from Example 1-C and a portion (0.0097 gram, 0.000179 hydroxyl equivalent) of 2,3,6,7,10,11-hexahydroxytriphenylene prepared using the method of Example 1-B were combined and ground together to a homogeneous powder. Differential scanning calorimetry of a portion (5.7 or 5.9 milligrams) of the product using a heating rate of 10° C. per minute, and a range from 30 to 275° C. under a stream of nitrogen flowing at a rate of 35 cubic centimeters per minute reveals an endotherm with a minimum at 125.7° C. and an enthalpy of 33.4 joules per gram, followed by an exotherm with a maximum at 181.3° C. and an enthalpy of 131.5 joules per gram (data averaged from two analysis). A second scanning reveals only a gradual exothermic rise commencing at 236° C. A third scanning reveals only a gradual exothermic rise commencing at 246° C. The cured product from the differential scanning calorimetry analysis was a fused, rigid black solid. Optical microscopic examination of the cured product from the differential scanning analysis under crosspolarized light reveals a high degree of birefringence around the edges of the sample with no crystals or domains apparent. The entire sample reveals a high degree of birefringence when fractured to give thin, light transmitting pieces. The birefringence observed was a bright orange red color throughout the product.

A portion of the curable blend was placed on a glass microscope slide, covered with a glass coverslip, then placed on the hot stage of an optical microscope. Heating commences at a rate of 10° C. per minute while the sample was observed under crosspolarized light. At 119° C., the first fluidity was observed. At 129° C., a birefringent melt was obtained which exhibits stir opalescence and grainy appearing domains. At 137° C., viscosity of the opalescent fluid increases. At 148° C., thermosetting occurs and the sample remains opalescent and birefringent and entirely composed of grainy appearing domains.

EXAMPLE 3

Preparation and Characterization of a Curable Mixture and Cured Composition Thereof Based on 2,3,6,7,10,11-Hexaglycidyloxytriphenylene and Polyoxypropylene Diamine A portion (0.0069 gram, 0.000052 epoxide equivalent) of the 2,3,6,7,10,11-hexaglycidyloxytriphenylene from Example 1-C and a portion (0.0030 gram, 0.000052 N—H equivalent) of polyoxypropylene diamine having a 57.5 N—H equivalent weight were directly weighed into an aluminum pan used for differential scanning calorimetry. A second sample was prepared exactly as per the above. Differential scanning calorimetry of the two samples (9.9 milligrams per sample) using a heating rate of 10° C. per minute, and a range from 30° to 275° C. under a stream of nitrogen flowing at a rate of 35 cubic centimeters per minute reveals an exotherm with a maximum at 114.3° C. and an enthalpy of 218.3 joules per gram (data averaged from two analysis). A second scanning reveals only a gradual exothermic rise commencing at 243° C. A third scanning reveals only a gradual exothermic rise commencing at 261° C. The cured product from the differential scanning calorimetry analysis was a fused, rigid, tough, amber colored solid. Optical microscopic examination of the cured product from the differential scanning analysis under crosspolarized light reveals a high degree of birefringence with no crystals or domains apparent but with localized regions of nematic texture present. The birefringence observed was a bright orange red color throughout the product, except in the regions which exhibit the nematic texture.

A portion of the curable blend was placed on a glass microscope slide, covered with a glass coverslip, then placed on the hot stage of an optical microscope. Heating commences at a rate of 10° C. per minute while the sample was observed under crosspolarized light. At 119° C., the first fluidity was observed. At 129° C., a birefringent melt was obtained which exhibits stir opalescence and grainy appearing domains. At 137° C., viscosity of the opalescent fluid increases. At 148° C., thermosetting occurs and the sample remains opalescent and birefringent and entirely composed of grainy appearing domains.

EXAMPLE 4

A. Synthesis of 2,8,14,20-Tetramethylpentacyclo $[19.3.1.1^{3,7}.1^{9,13}.1^{15,19}]$-octacosa-1(25),3,5,7(28),9, 11,13(27),15,17,19(26),21,23-dodecaene-4,6,10,12,-16,18,22,24-octol Resorcinol (55.05 grams, 0.50 mole) and ethanol (250 milliliters) were added to a reactor and stirred under a nitrogen atmosphere to provide a solution. Deionized water (250 milliliters) and concentrated hydrochloric acid (112.5 milliliters) were sequentially added to the stirred solution followed by cooling in an ice water bath to 15° C. After the 15° C. temperature was achieved, acetaldehyde (22.01 grams, 0.05 mole) was added dropwise to the reactor over a 21 minute period and so as to maintain the 15° C. temperature. Three minutes after completion of the acetaldehyde addition, the temperature had decreased to 13° C. and the ice water bath was removed and the temperature allowed to increase. After 15 minutes, the temperature had reached 20° C. and heating commenced. After 21 minutes, a temperature of 42° C. was achieved and the reaction product appeared as a yellow solution. After an additional 7 minutes, a 50° C. temperature was achieved and was maintained therein. After 23 minutes at the 50° C. temperature, the yellow solution became hazy. After a total of one hour at the 50° C. temperature, a slurry was present and heating ceased. After cooling to room temperature (23–25° C.), the stirred slurry was maintained under the nitrogen atmosphere for the next 4 days. After this time, the reaction slurry was filtered and the white crystalline product recovered on the filter was recrystallized from a 50/50v/v solution of ethanol/deionized water (950 milliliters). The solid was recovered from the recrystallization by filtration then dried in a vacuum oven at 60° C. and one mm Hg to a constant weight. (A second crop of crystals which formed in the filtrate was discarded). A second recrystallization of the dried solid was completed by boiling in acetonitrile (100 milliliters) followed by cooling to room temperature. After 4 hours at room temperature, the crystalline product recovered on the filter was dried in a vacuum oven at 60° C. and one mm Hg to a constant weight 18.0 grams of white crystals. A second crop (6.3 grams) of white crystals were recovered by partial evaporation of the acetonitrile from the filtrate. Differential scanning calorimetry was completed using portions (13.1 and 14.0 milligrams) of the product and a heating rate of 10° C. per minute under a stream of nitrogen flowing at 35 cubic centimeters per minute and a temperature from 30° C. to 500° C. An pair of endotherms were obtained with minima at 191.2° C. and 355.6° C. and enthalpies of 99.1 and 371.5 joules per gram, respectively (average of two samples). Fourier transform infrared spectrophotometric analysis of a potassium bromide pellet of the product reveals the presence of the expected strong, broad phenolic O—H stretching absorption centered at 3316 cm$^{-1}$, the aromatic C—O stretching absorption centered at 1264 cm$^{-1}$ with multiple shoulders, aromatic ring C—H stretching vibration at 3037 cm$^{-1}$, aromatic ring C=C stretching vibrations at 1616, (1596 shoulder), 1503 and 1437 cm$^{-1}$, aromatic ring out-of-plane C—H bending vibration at 832 cm$^{-1}$ (with shoulders at 846 and 852 cm$^{-1}$) indicative of 1,2,4,5- tetrasubstitution and C—H stretching absorptions at 2971, 2938 and 2878 cm$^{-1}$.

B. Partial Esterification of 2,8,14,20-Tetramethylpentacyclo[19.3.1.1$^{3,7}$-1$^{9,13}$,1$^{15,19}$] octacosa-1(25),3,5,7(28),9,11,13(27),15,17,19(26), 21,23- dodecaene-4,6,10,12,16,18,22,24-octol A portion (3.404 grams, 0.05 hydroxyl equivalent) of 2,8,14,20-tetramethylpentacyclo[19.3.1.1$^{3,7}$.1$^{9,13}$.1$^{15,19}$] octacosa-1(25),3,5,7(28),9,11,13(27),15,17,19(26),21,23-dodecaene-4,6,10,12,16,18,22,24-octol from A. above, palmitoyl chloride (6.872 grams, 0.025 mole) and tetrachloroethylene (250 milliliters) were added to a reactor and stirred under a nitrogen atmosphere with heating. Once a temperature of 110° C. was achieved, the reactor was maintained therein for the next 16 hours. The solution was recovered and rotary evaporated at 100° C. and 1 mm of Hg to a constant weight of a waxy white solid product. Fourier transform infrared spectrophotometric analysis of a potassium bromide pellet of the product revealed the expected reduction in the phenolic O—H stretching absorption (centered at 3389 cm$^{-1}$) accompanied by the appearance of the ester carbonyl stretching absorption at 1736 cm$^{-1}$ (shoulder at 1762 cm$^{-1}$) and increase in the C—H stretching absorptions (2957, 2924 and 2858 cm$^{-1}$).

C. Epoxidation of Partially Esterified 2,8,14,20-Tetramethylpentacyclo-[19.3.1.1$^{3,7}$,1$^{9,13}$,1$^{15,19}$] octacosa-1(25),3,5,7(28),9,11,13(27),15,17,19(26),- 21,23-dodecaene-4,6,10,12,16,18,22,24-octol The partially esterified 2,8,14,20-tetramethylpentacyclo [19.3.1.1$^{3,7}$,-1$^{9,13}$,1$^{15,19}$]octacosa-1(25),3,5,7(28),9,11,13 (27),15,17,19(26),21,23-dodecaene-4,6,10,12,16,18,22,24-octol from B above (less a trace of sample removed for the infrared spectrophotometric analysis) dissolved in epichlorohydrin (231.3 grams, 2.5 moles) was added to a glass three necked round bottom reactor and stirred under a nitrogen atmosphere as a solution. Tetra-n-butylammonium bromide (0.094 gram) was added, then heating commenced until a temperature of 80° C. was achieved. After 117 minutes at the 80° C. temperature, a sample of the solution was taken and found to be substantially insoluble in acetonitrile. After 8 hours at the 80° C. temperature, a sample of the hazy solution was taken and found to be much more, although not completely, soluble in acetonitrile. After 23.35 hours at the 80° C. temperature, a sample was taken and found to be completely soluble in acetonitrile. At this time, a water separator was interspersed between the reactor and the chilled (–2.5° C.) glycol condenser and an addition funnel containing sodium hydroxide (1.125 gram, 0.028 mole) dissolved in deionized water (1.38 milliliters, 55% wt. of the solution) and a vacuum line were added to the reactor. The nitrogen purge was shut off simultaneously with the initiation of the vacuum. The vacuum and reaction temperature were equilibrated at 50° C. and 110 mm Hg, respectively, and such that a vigorous reflux was maintained with continuous return of dry epichlorohydrin from the water separator. After equilibration, dropwise addition of the aqueous sodium hydroxide commenced with maintainance of the reaction temperature and vacuum. After 10 minutes, addition of the aqueous sodium hydroxide was complete. After an additional 3 hours at the aforementioned reaction temperature and vacuum, heating ceased and the recovered warm product slurry was filtered through a bed of diatomaceous earth. The recovered filtrate was added to a separatory funnel then washed with two portions (150 milliliters) of deionized water. The recovered organic layer was dried over anhydrous sodium sulfate, filtered, then rotary evaporated under a vacuum (1 mm Hg final condirtions) at 110° C. for 3 hours to a constant weight of 12.70 grams of a tacky, white, semisolid at room temperature (23° C.). Titration of a portion of this product reveals the presence of 12.29% epoxide (350.38 epoxide equivalent weight). Infrared spectrophotometric analysis of a potassium bromide pellet of the product reveals the disappearance of the O—H stretching absorption (centered at 3389 cm$^{-1}$) concurrent with maintenance of the ester carbonyl stretching absorption at 1742 cm$^{-1}$, the aromatic ring C—H stretching vibration at 3057 cm$^{-1}$, aromatic ring C=C stretching vibrations at 1609, 1583, 1503 and 1457 cm$^{-1}$, C—H stretching absorptions at 2971, 2938 and 2878 cm$^{-1}$, the aromatic ring C—O vibration for the ether linkage at 1297 cm$^{-1}$, the aliphatic portion of the C—O vibration for the ether linkage at 1038 cm$^{-1}$, the aromatic ring C—O stretching vibration at 1118 cm$^{-1}$, the epoxide ring C—O stretching vibration at 912 cm$^{-1}$ and the C—H out-of-plane vibration for the aromatic rings at 846

(increased absorption due to overlap with epoxide ring vibration expected at 835 cm$^{-1}$).

EXAMPLE 5

Preparation and Copolymerization of a Curable Mixture Based on 2,8,14,20-Tetramethylpentacyclo [19.3.1.1$^{3,7}$.1$^{9,13}$.1$^{15,19}$]-octacosa-1(25),3,5,7(28),9, 11,-13(27),15,17,19(26),21,23-dodecaene-4,6,10,12, 16,18,22,24-octol and the Epoxy Resin of Partially Esterified 2,8,14,20-Tetramethylpentacyclo[19.3.-1.1$^{3,7}$,1$^{9,13}$,1$^{15,19}$]-octacosa-1(25),3,5,7(28),9,11,13 (27),15,17,19(26),-21,23-dodecaene-4,6,10,12,16,18, 22,24-octol A portion (0.7138 gram, 0.0020 epoxide equivalent) of the epoxy resin of partially esterified 2,8,14,20-tetramethylpentacyclo[19.3.1.1$^{3,7}$,1$^{9,13}$,-1$^{15,19}$]octacosa-1 (25),3,5,7(28),9,11,13(27),15,17,19(26),-21,23-dodecaene-4,6,10,12,16,18,22,24-octol from Example 4-C and a portion (0.13868 gram, 0.0020 hydroxyl equivalent) of 2,8,14,20-tetramethylpentacyclo[19.3.1.1$^{3,7}$.-1$^{9,13}$.1$^{15,19}$] octacosa-1(25),3,5,7(28),9,11,13(27),-15,17,19(26),21,23-dodecaene-4,6,10,12,16,18,22,24-octol from Example 4-A were dissolved in acetone (20 milliliters). The acetone was allowed to evaporate under a stream of nitrogen, followed by drying of the curable mixture at 50° C. and 1 mm Hg to a constant weight. Differential scanning calorimetry of a portion (9.3 or 18.7 milligrams) of the curable mixture using a heating rate of 10° C. per minute, and a range from 30° to 400° C. under a stream of nitrogen flowing at a rate of 35 cubic centimeters per minute revealed a pair of exotherms with maxima at 193.1° C. and 343.7° C. and enthalpies of 11.8 and 136.9 joules per gram, respectively (data averaged from two analysis). A second scanning revealed an apparent glass transition temperature at 360.5° C. The cured product from the differential scanning calorimetry analysis was a fused, tough, clear light amber colored solid. Optical microscopic examination of the cured product from the differential scanning analysis under crosspolarized light at 70× magnification revealed a high degree of birefringence. Thin sections of the product appear to be composed of birefringent spherical structure which was closely packed together.

A portion (0.7138 gram, 0.0020 epoxide equivalent) of the epoxy resin of partially esterified 2,8,14,20-tetramethylpentacyclo[19.3.1.1$^{3,7}$,1$^{9,13}$,-1$^{15,19}$]octacosa-1 (25),3,5,7(28),9,11,13(27),15,17,19(26),-21,23-dodecaene-4,6,10,12,16,18,22,24-octol from Example 4-C and a portion (0.13868 gram, 0.0020 hydroxyl equivalent) of 2,8,14,20-tetramethylpentacyclo[19.3.1.1$^{3,7}$.-1$^{9,13}$.1$^{15,19}$] octacosa-1(25),3,5,7(28),9,11,13(27),-15,17,19(26),21,23-dodecaene-4,6,10,12,16,18,22,24-octol from Example 4-A were dissolved in acetone (20 milliliters), followed by the addition of tetra-n-butylphosphonium fluoroborate (2 milliequivalents per epoxide equivalent). The acetone was allowed to evaporate under a stream of nitrogen, followed by drying of the curable mixture at 50° C. and 1 mm Hg to a constant weight. The resulting mixture was then B-staged at 50° C. for 15 hours to provide a homogeneous pale tan wax. Differential scanning calorimetry of a portion (19.0 or 18.7 milligrams) of the B-staged mixture using a heating rate of 10° C. per minute, and a range from 30° to 300° C. under a stream of nitrogen flowing at a rate of 35 cubic centimeters per minute revealed a pair of overlapping exotherms with maxima at 159.3° C. and 201.7° C., respectively with a total enthalpy of 61.2 joules per gram (data averaged from two analysis). A second scanning reveals no events up to 300° C. The cured product from the differential scanning calorimetry analysis was a fused, tough, clear light amber colored solid. Optical microscopic examination of the cured product from the differential scanning analysis under crosspolarized light at 70× magnification reveals a high degree of birefringence. Thin sections of the product appear to be composed of birefringent spherical structure which was closely packed together.

We claim:

1. An epoxy resin containing an average of more than one vicinal epoxide group per molecule characterized by containing at least one discotic mesogenic moiety per molecule represented by the following formulas VII–XII Formula VII (M—Z$^3$)$_p$—D Formula VIII (M—Z$^3$)$_p$$^1$—D—[(Q$_n$—R$^1$)$_m$$^1$—Q$_n$—R]$_m$ Formula IX D—[(Q$_n$—R$^1$)$_m$$^1$—Q$_n$—Ar—Z$^3$—M]$_p$ Formula X (M—Z$^3$)$_p$$^1$—D—[(Q$_n$—R$^1$)$_m$$^1$—Q$_n$—Ar—Z$^3$—M]$_m$ Formula XI D—[(Q$_n$—R$^1$)$_m$$^1$—(Q$_n$—Ar)$_n$—Q$_n$—Z$^4$]$_p$ Formula XII (Z$^4$—Q$_n$)$_p$$^1$—D—[(Q$_n$—R$^1$)$_m$$^1$—Q$_n$—R]$_m$ wherein Ar is a benzene, naphthalene or biphenyl moiety having from 6 to about 12 carbon atoms; D is a disk-shaped core selected from the group consisting of triphenylenes, azatriphenylenes, hexa(4-substituted benzoates) of triphenylene, alkyl or substituted alkyl pentakis (phenylethynyl)phenyl ethers, multi((phenyl)alkynyl) triphenylenes, hexakis((phenyl)alkynyl)benzenes, hexakis ((phenyl)alkynyl)naphthalenes, hexa(4-substituted benzoates) of benzene, hexakis(aryloxy)benzenes, truxenes, trithiatruxenes, trioxatruxenes, triazatruxenes, triketotruxenes, phthalocyanines, metallophthalocyanines, porphyrins, metalloporphyrins, macrocyclic polyamines, cyclomultibenzylenes, metacyclophanes, anthraquinones, tricycloquinazoline, bipyranylidenes, triptycenes, bis[1,2-bis(phenyl)ethane-1,2-dithiolato]metals, bis(β-diketonato) metal complexes, triaryl pyrylium salts, decacyclenes, dibenzopyrenes, tungstenoxocalix[4]arenes and cis,cis-(3,5-dihydroxycyclohexyl)-3,4,5-tri(substituted)-benzoates; each Q is independently a —O—CO—, —CO—O—, —CO—NR$^1$—, —NR$^1$—CO—, —S—CO—, —CO—S—, —O—CO—O—, —NR$^1$—CO—NR$^1$—, —NR$^1$—CO—O—, O—CO—NR$^1$—, —O—, —S—, —S—S—, —SO$_2$—, or —CO— group; R is a monovalent hydrocarbyl group having from 1 to about 20 carbon atoms; R$^1$ is a divalent hydrocarbyl group having from 1 to about 20 carbon atoms; each R$^a$ is independently hydrogen or an alkyl or haloalkyl group with the proviso that only one R$^a$ group can be a haloalkyl group; m has a value from 1 to about 20; m$^1$ has a value from zero to about 5; n has a value of zero or 1; p has a value from 3 to about 20; p$^1$ has a value from 1 to about 20; each M is independently a

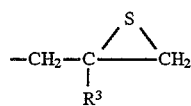

group; R$^3$ is hydrogen or a monovalent hydrocarbyl group having one to about 3 carbon atoms; each Z$^3$ is independently (a) a —O—, —S—, —NR—, —N<, or —CO—O— group where the single bonded oxygen atom attached to the carbon atom of —CO—O— is attached to the group represented by M, or (b) a —O—(CHR$^a$—CHR$^a$—O)$_p^3$—, —CO—O—(CHR$^a$—CHR$^a$—O)$_p^3$—, —S—(CHR$^a$—CHR$^a$—O)$_p^3$—, —NR—(CHR$^a$—CHR$^a$—O)$_p^3$—, or —N—((CHR$^a$—CHR$^a$—O)$_p^3$—)$_2$ group where the single bonded oxygen atom is attached to the group represented by M; $Z^4$ is an epoxidized olefinically unsaturated group having from 2 to about 20; $p^3$ has a value of one to about 100 with the proviso the sum of $p^1$ and m in Formulas VIII, X, or XII must have a value of at least about 3 or more; and with the proviso that said epoxy resin is not an epoxy resin represented by the formula

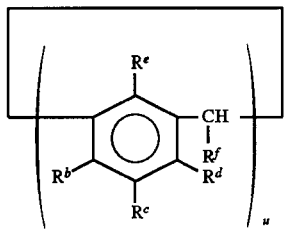

where $R^b$ and $R^d$ are either the same or difference and are selected from hydrogen, hydroxyl, alkoxy, alkenyloxy and epoxypropyloxy (glycidyloxy); $R^c$ is selected from hydrogen, halogen, alkenyl, alkyl optionally substituted with halogen, arylalkyl optionally substituted with halogen, and aryl optional substituted with halogen; $R^f$ is selected from hydrogen, alkyl optionally substituted with halogen, arylalkyl optionally substituted with halogen and aryl optionally substituted with alkyl or halogen or both; $R^e$ is selected from hydrogen, halogen, alkyl or alkenyl; u is an integer from 3 to 10; and with the proviso that at least one epoxypropyloxy (glycidyloxy) group per molecule is present; and wherein said discotic mesogenic moiety is composed of a disk-shaped, rigid, essentially planar core to which flexible aliphatic chains or tails may be attached and intermolecular attraction between the disk-like core structures and hydrophobic interaction between the aliphatic chains or tails are such that long range three dimensional order is precluded.

2. The epoxy compound 2,3,6,7,10,11-hexaglycidyloxytriphenylene.

* * * * *